United States Patent [19]
Kirschling et al.

[11] Patent Number: 5,942,389
[45] Date of Patent: Aug. 24, 1999

[54] GENES AND GENETIC ELEMENTS ASSOCIATED WITH SENSITIVITY TO CISPLATIN

[75] Inventors: Deborah J. Kirschling, Hanover Park; Andrei Gudkov, Chicago; Igor B. Roninson, Wilmette, all of Ill.

[73] Assignee: Board of Trustees of the University of Illinois, Urbana, Ill.

[*] Notice: This patent is subject to a terminal disclaimer.

[21] Appl. No.: 08/485,657

[22] Filed: Jun. 7, 1995

Related U.S. Application Data

[62] Continuation of application No. 08/199,900, Feb. 22, 1994, abandoned, which is a continuation-in-part of application No. 08/033,086, Mar. 9, 1993, abandoned, which is a continuation-in-part of application No. 07/599,730, Oct. 19, 1990, Pat. No. 5,217,889, said application No. 08/199,900, is a continuation-in-part of application No. 08/039,385, filed as application No. PCT/US91/07492, Oct. 11, 1991, Pat. No. 5,811,234, which is a continuation-in-part of application No. 07/599,730.

[51] Int. Cl.⁶ .............. C12Q 1/68; C12N 15/00; C12N 5/06; C07H 21/04
[52] U.S. Cl. ............ 435/6; 435/172.3; 435/366; 536/23.5; 536/24.1; 536/24.5
[58] Field of Search ............ 435/6, 172.3, 366; 536/23.5, 24.1, 24.5

[56] References Cited

U.S. PATENT DOCUMENTS

| | | | |
|---|---|---|---|
| 4,689,320 | 8/1987 | Kaji | 514/44 |
| 5,217,889 | 6/1993 | Roninson et al. | 435/172.3 |

FOREIGN PATENT DOCUMENTS

| | | |
|---|---|---|
| WO-A-8803558 | 5/1988 | WIPO. |

OTHER PUBLICATIONS

Groger, et al. 1989. "Directional antisense and sense cDNA cloning using Epstein–Barr virus episomal expression vectors." Gene 81:285–294.

Lock, et al. 1988. "Differential patterns of anti–tumor drug responses and mechanisms of resistance in a series of independently–derived VP–16–resistant human tumour cell lines." Int. J. Cancer 42(3):371–381.

Patanjali, et al. 1991. "Construction of a uniform–abundance (normalized) cDNA library." Proc. Natl. Acad. Sci. USA 88:1943–1947.

Shen, et al. 1986. "Human multidrug–resistant cell lines: Increased mdrl expression can precede gene amplification." Science 232:643–645.

Tsai–Pflugfelder, et al. 1988. Cloning and sequencing of cDNA encoding human DNA topoisomerase II and localization of the gene to chromosome region 17q21–22. Proc. Natl. Acad. Sci. USA 85:7177–7181.

Uhlmann, et al. 1990. "Antisense oligonucleotides: A new therapeutic principle." Chem. Rev. 90(4):543–584.

Holzmayer, et al. 1992. Isolation of dominant negative mutants and inhibitory antisense RNA sequences by expression selection of random DNA fragments. Nuc. Acids Res. 20(4):711–717.

Sczakiel, G. Et al. Jun. 15, 1990. Specific inhibition of human immunodeficiency virus type I replication by RNA transcribed in sense and antisense orientation from the 5'–leader/gag region, Bioch. Biophys. Res. Comm. 169 (2):643–651.

Friedman, A.D. et al. Sep. 29, 1988. "Expression of a truncated viral transactivator selectively impedes lytic infection by its cognate virus", Nature 335:452–454.

Napoli, C., et al. Apr., 1990. "Introduction of a chimeric chalcone synthase gene into petunia results in reversible co–suppression of homologus genes in trans", The Plant Cell 2(4):279–289.

Kidd, V.J., et al. Dec. 4, 1990. "Dominant negative mutation in galactosyltransferase created by over–expression of a truncated cDNA", Chemical Abstracts 111(23):225–234.

Baird, L., et al. Mar. 1990. "Identification, cloning, and characterization of the Escherichia coli sohA gene, a suppressor of the htrA (degP) Null phenotype", Journal of Bacteriology 172(3):1587–1594.

Chen, et al., 1986, "Internal Duplication and Homology with Bacterial Transport Proteins in the mdrl (P–glycoprotein) Gene from Multidrug–Resistant Human Cells", Cell 47:381–389.

Noonan, et al., 1990, "Quantitative Analysis of MDR1 (multidrug resistance) gene expression in human tumors by polymerase chain reaction", Proc. Natl. Acad. Sci. USA 87:7160–7164.

Holzmayer, et al., 1992, "Isolation of dominant negative mutants and inhibitory antisense RNA sequences by expression selection of random DNA fragments", Nuc. Acids Res. 20:711–717.

Culver, et al., 1992, "In Vivo Gene Transfer with Retroviral Vector–Producer Cells for Treatment of Experimental Brain Tumors", Science 256:1550–1552.

Gudkov, et al., 1993, "Isolation of genetic suppressor elements inducing resistance to topoisomerase II–interactive cytotoxic drugs, from human topoisomerase II cDNA", Proc. Natl. Acad. Sci. USA 90:3231–3235.

Sakod et al. The Journal of Biological Chemistry, 263(32):16899–16905, 1988.

Minet et al. Gene. 121:393–396, 1992.

Maniatis et al, (1982) Molecular Cloning: A Laboratory Manual. CSH Laboratory Press, CSH N.Y. p. 270–271.

Groger et al. (1989) Gene 81, 285–294.

Scanlon et al. (1988) PNAS, USA 85, 650–653.

Shen et. al (1986) Science 232, 643–645.

Holzmayer et. al (1992) Nucleic Acids Res. 20, 711–717.

Uhlmann et. al, (1990) Chem. Rev. 90, 543–584.

Milligan et al. (1993) J. Med. Chem. 36(14), 1923–1937.

Lau and Nathans, 1985, "Identification of a set of genes expressed during the G0/G1 transition of cultured mouse cells", EMBO J. 4: 3145–3151.

Chen et al., 1986, "Internal Duplication and Homology with Bacterial Transport Proteins in the mdr1 (P–Glycoprotein) Gene from Multidrug–Resistant Human Cells", Cell 47: 381–389.

Krusius & Ruoslahti, 1986, "Primary structure of an extracellular matrix proteoglycan core protein deduced from cloned cDNA", Proc. Natl. Acad. Sci. USA 83: 7683–7687.

Lau and Nathans, 1987, "Expression of a set of growth–related immediate early genes in BALB/c 3T3 cells: Coordinate regulation with c–fos or c–myc", Proc. Natl. Acad. Sci. USA 84: 1182–1186.

Vale, 1987, "Intracellular transport using microtubule–based motors", Ann. Rev. Cell Biol. 3: 347–378.

Bender et al., 1987, "Evidence that the Packaging Signal of Moloney Murine Leukemia Virus Extends into the gag Region", J. Virol. 61: 1639–1646.

Richon et al., 1987, "Multiple Mechanisms of Resistance to cis–Diamminedichloroplatinum(II) in Murine Leukemia L1210 Cells", Cancer Res. 47: 2056–2061.

Kelley et al., 1988, "Overexpression of Metallothionein Confers Resistance to Anti cancer Drugs", Science 241: 1813–1815.

Sklar, 1988, "Increased Resistance to cis–Diamminedichloroplatinum(II) in NIH 3T3 cells Transformed by ras Oncogenes", Cancer Res. 48: 793–797.

Sakoda et al., 1988, "Isolation of a cDNA Encoding the B Isozyme of Human Phosphoglycerate Mutase (PGAM) and Characterization of the PGAM Gene Family", J. Biol. Chem. 263: 16899–16905.

Yamaguchi & Ruoslahti, 1988, "Expression of human proteoglycan in Chinese hamster ovary cells inhibits cell proliferation", Nature 336: 244–246.

Markowitz et al., 1988, "Construction and Use of a Safe and Efficient Amphotropic Packaging Cell Line", Virology 167: 400–406.

Ohara et al., 1989, "One–sided polymerase chain reaction: the amplification of cDNA", Proc. Natl. Acad. Sci. USA 86: 5673–5677.

Albritton et al., 1989, "A Putative Murine Ecotropic Retrovirus Receptor Gene Encodes a Multiple Membrane–Spanning Protein and Confers Susceptibility to Virus Infection", Cell 57: 659–666.

Miller and Rosman, 1989, "Improved Retroviral Vectors for Gene transfer and Expression", Biotechniques 7: 980–986.

McConkey et al., 1989, "Glucocorticoids Activate a Suicide Process in Thymocytes through an Elevation of Cytosolic $Ca^{2+}$ Concentration", Arch. Biochem. Biophys. 269: 365–370.

Reed et al., 1989, "Expression of the human DNA repair gene ERCC–1 relates to cisplatin drug resistance in human ovarian cancer cells", Proc. Amer. Assoc. Cancer Res. 30: 488.

Eastman, 1990, "Activation of Programmed Cell Death by Anticancer Agents: Cisplatin as a Model System", Cancer Cells 2: 275–2802.

Bernal et al., 1990, "Reduced membrane protein associated with resistance of human squamous carcinoma cells to methotrexate and cis–platinum", Mol. Cell. Biochem. 95: 61–703.

Kawai et al., 1990, "Identification of a Membrane Gylcoprotein Overexpressed in Murine Lymphoma Sublines Resistant to cis–Diamminedichloroplatinum(II)", J. Biol. Chem. 265: 13137–13142.

Schilder et al., 1990, "Metallothionein Gene Expression and Resistance to Cisplatin in Human Ovarian Cancer", Int. J. Cancer 45: 416–422.

Miyazaki et al., 1990, "Drug Resistance to cis–Diamminedichloroplatinum(II) in Chinese Hamster Ovary Cell Lines Transfected with Glutathione S–Transferase Pi Gene", Biochem. Biophys. Res. Commun. 166: 1358–1364.

Nakagawa et al., 1990, "Glutathione–S–Transferase π as a Determinant of Drug Resistance in Transfected Cell Lines", J. Biol. Chem. 265: 4296–4301.

Chu & Chang, 1990, "Cisplatin–resistant cells express increased levels of a factor that recognizes damaged DNA", Proc. Natl. Acad. Sci. USA 87: 3324–3328.

Yamaguchi et al., 1990, "Negative regulation of transforming growth factor–β by the proteoglycan decorin", Nature 346: 281–2884.

Altshul et al., 1990, "Basic Local Alignment Search Tool", J. Mol. Biol. 215: 403–410.

Thompson et al., 1990, "Molecular Cloning of a Human XRCC1 Gene, Which Corrects Defective DNA Strand Break Repair and Sister Chromatid Exchange", Mol. Cell. Biol. 10: 6160–6171.

Noonan et al., 1990, "Quantitative analysis of MDR1 (multidrug resistance) gene expression in human tumors by polymerase chain reaction", Proc. Natl. Acad. Sci. USA 87: 7160–7164.

Kung et al., 1990, "Cytotosic Effects of Cell Cycle Phase Specific Agents: Result of Cell Cycle Perturbation", Cancer Res. 50: 7307–7317.

Uhlmann and Peyman, 1990, "Antisense Oligonucleotides: A New Therapeutic Principle", Chemical Reviews 90: 543–584.

Schneider and Banner, 1990, "Building blocks for oligonucleotide analogs with dimethylene–sulfide, –sulfoxide, and –sulfone groups replacing phosphodiester linkages", Tetrahedron Letters 31: 335.

Bodine et al., 1990, "Development of high–titer retrovirus producer cell line capable of gene transfer into rhesus monkey hematopoietic stem cells", Proc. Natl. Acad. Sci. USA 87: 3738–3742.

Baim et al., 1991, "A chimeric mammalian transactivator based on the lac repressor that is regulated by temperature and isopropyl β–D–thiogalactopyranoside", Proc. Natl. Acad. Sci. USA 88: 5072–5076.

Patanjali et al., 1991, "Construction of a uniform–abundance (normalized) cDNA library", Proc. Natl. Acad. Sci. USA 88: 1943–1947.

Buttyan, 1991, "Genetic Response of Prostate Cells to Androgen Deprivation: Insights into the Cellular Mechanisms of Apoptosis", in *Apoptosis. The Molecular Basis of Cell Death*, Tomei & Cope, eds., Cold Spring Harbor Laboratory Press, Cold Spring Harbor, NY, pp. 157–173.

Chao et al., 1991, "Cross–Resistance to UV Radiation of a Cisplatin–Resistant Human Cell Line: Overexpression of Cellular Factors that Recognize UV–Modified DNA", *Mol. Cell. Biol.* 11: 2075–2080.

Leyland–Jones et al., 1991, "Antineoplastic Drug Sensitivity of Human MCF–7 Breast Cancer Cells Stably Transfected with a Human α Class Glutathione–S–Transferase Gene", *Cancer Res.* 51: 587–594.

Isonishi et al., 1991, "Expression of the c–Ha–ras Oncogene in Mouse NIH 3T3 Cells Induces Resistance to Cisplatin", *Cancer Res.* 51: 5903–5909.

Niimi et al., 1991, "Resistance to anticancer drugs in NIH3T3 cells transfected with c–myc and/or c–H–ras genes", *Br. J. Cancer* 63: 237–241.

Scanlon et al., 1991, "Ribozyme–mediated cleavage of c–fos mRNA reduces gene expression of DNA synthesis enzymes and metallothionein", *Proc. Natl. Acad. Sci. USA* 88: 10591–10595.

Townsend et al., 1992, "Expression of Human μ or α Class Glutathione S–Transferases in Stably Transfected Human MCF–7 Breast Cancer Cells: Effect on Cellular Sensitivity to Cytotoxic Agents", *Mol. Pharmacol.* 41: 230–236.

Bruhn et al., 1992, "Isolation and characterization of human cDNA clones encoding a high mobility group box protein that recognizes structural distortions to DNA caused by binding of the anticancer agent cisplatin", *Proc. Natl. Acad. Sci. USA* 89: 2307–2311.

Minet et al., 1992, "Cloning and sequencing of a human cDNA coding for dihydroorotate dehydrogenase by complementation of the corresponding yeast mutant", *Gene* 121: 393–396.

Kikuchi et al., 1992. "Restorative Effects of Calmodulin Antagonists on Reduced Cisplatin Uptake by Cisplatin–Resistant Human Ovarian Cancer Cells", *Gynecol. Oncol.* 39: 199–203.

Kohnoe et al., 1992, "Intracellular Accumulation of Free Calcium in Mouse Tumor Cells Exposed to Anticancer Drugs", *Anticancer Res.* 12(6B): 2203–2207.

Culver et al., 1992, "In Vivo gene Transfer with Retroviral Vector–Producer Cells for Treatment of Experimental Brain Tumors", Science 256: 1550–1552.

Bramson & Panasci, 1993, "Effect of ERCC–1 Overexpression on Sensitivity of Chinese Hamster Ovary Cells to DNA Damaging Agents", *Cancer Res.* 53: 3237–3240.

Peters et al., 1993, "Transformation of Mouse Fibroblasts with the Oncogenes H–ras or trk is Associated with Pronounced Changes in Drug Sensitivity and Metabolism", *Int. J. Cancer* 54: 450–455.

Perez et al., 1993, "Transformation of Rat Ovarian Epithelial and Rat–1 Fibroblast Cell Lines by RAST24 Does Not Influence Cisplatin Sensitivity", *Cancer Res.* 53: 3771–3775.

Iozzo & Cohen, 1993, "Altered proteoglycan gene expression and the tumor stroma", *Experientia* 49: 447–455.

Nghiem et al., 1993, "Cloning and Analysis of Two New Isoforms of Multifunctional $Ca^{2+}$/Calmodulin–dependent Protein Kinase", *J. Biol. Chem.* 268: 5471–5479.

Gudkov et al., 1993, "Isolation of genetic suppressor elements, inducing resistance to topoisomerase II–interactive cytotoxic drugs, from human topoisomerase II cDNA", Proc. Natl. Acad. Sci. USA 90: 3231–3235.

*Primary Examiner*—Douglas W. Robinson
*Assistant Examiner*—Thanda Wai
*Attorney, Agent, or Firm*—McDonnell, Boehnen, Hulbert & Berghoff

[57] ABSTRACT

The invention provides genetic suppressor elements that confer upon a cell resistance to platinum-based drugs, including cisplatin, methods for identifying and obtaining such elements, and methods of using such elements. The invention also provides cloned genes associated with sensitivity to cisplatin.

27 Claims, 32 Drawing Sheets

Figure 4B
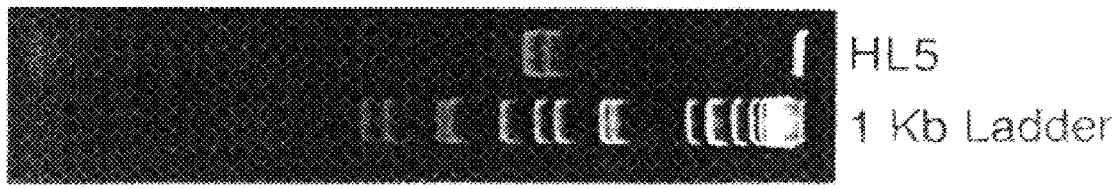

Figure 5C
LNCX
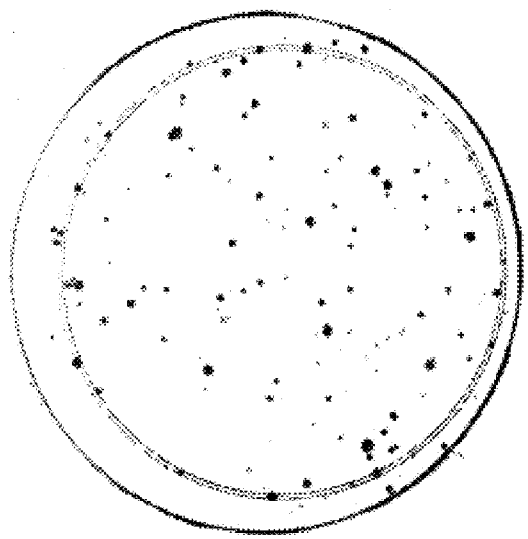
HL6.1
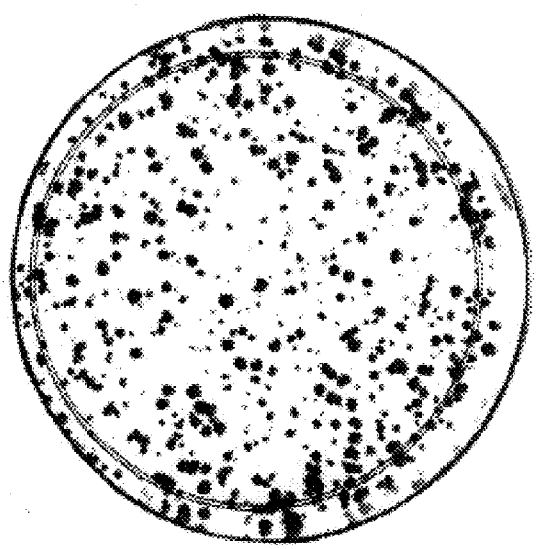
HL6.10
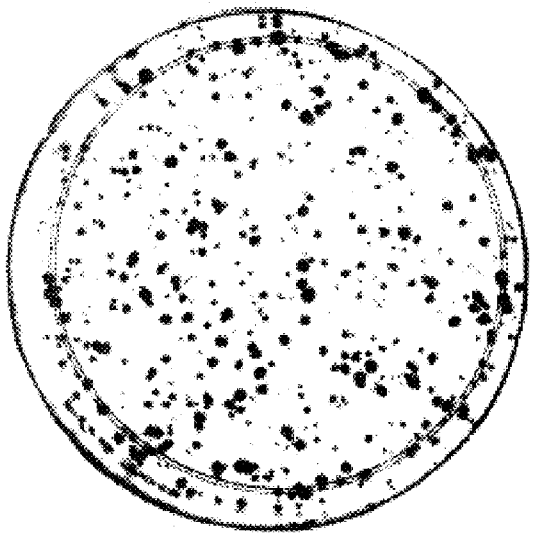

Figure 5D
LNCX
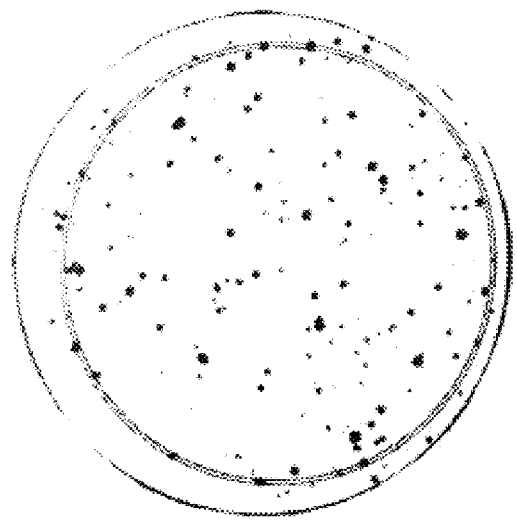
H63.C8
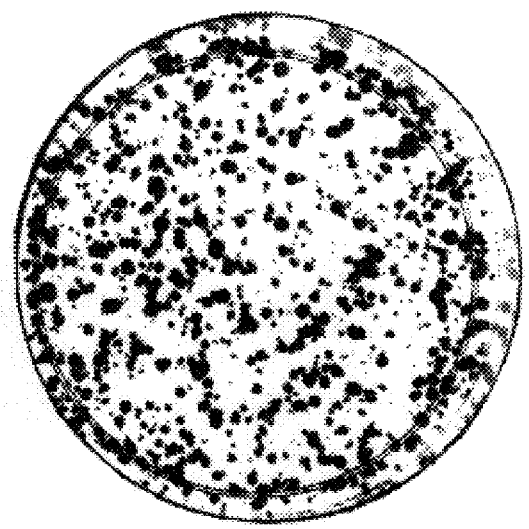
HL4.1
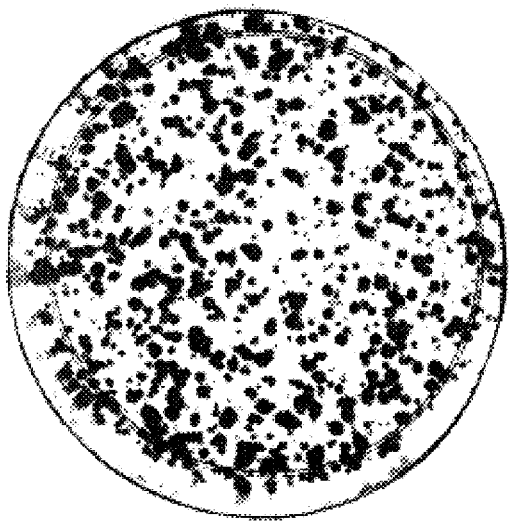

Figure 5E
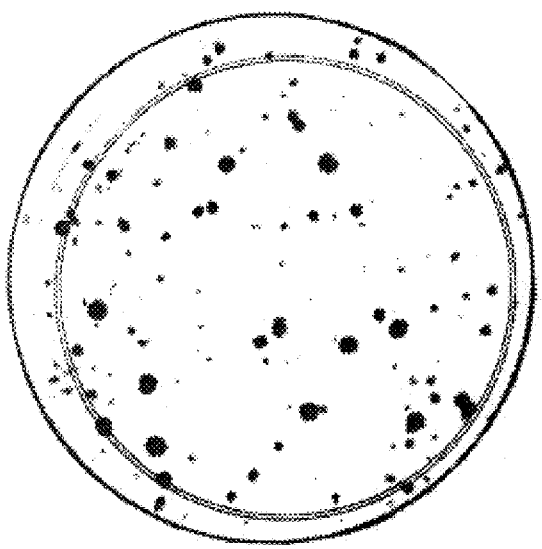
LNCX
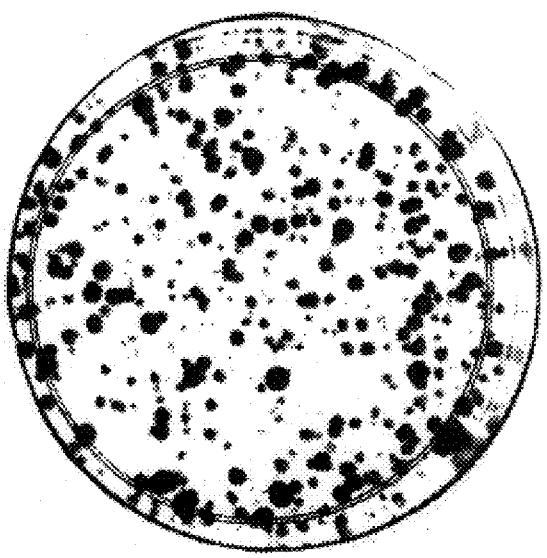
H91.E2
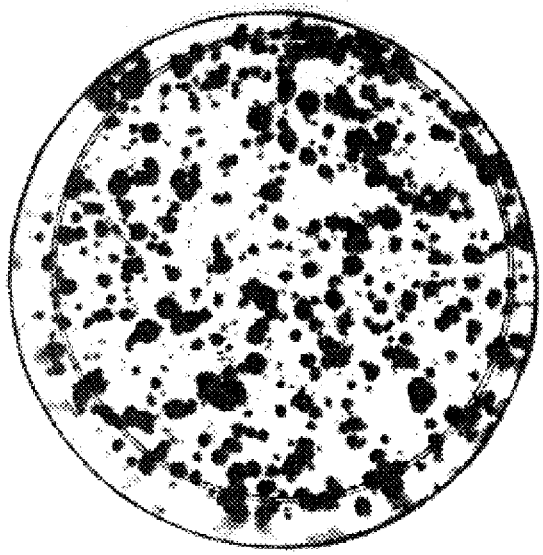
H91.E4
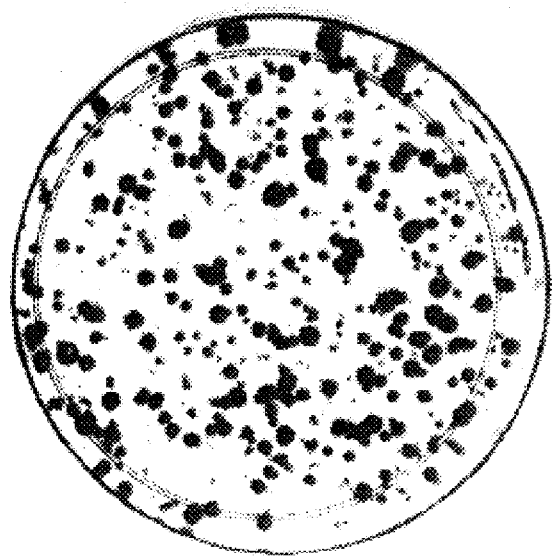
H93.G6

Figure 5F
LNCX
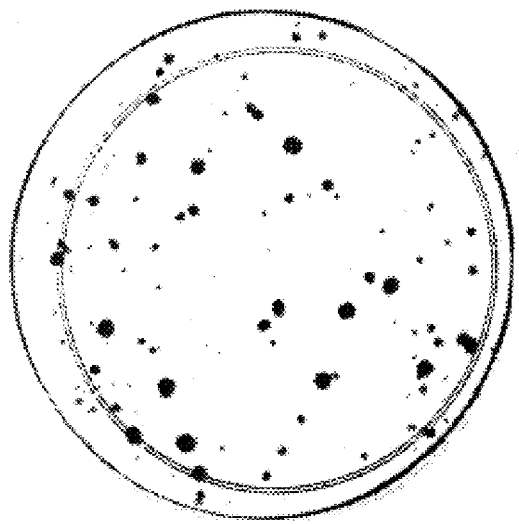
H62.B2
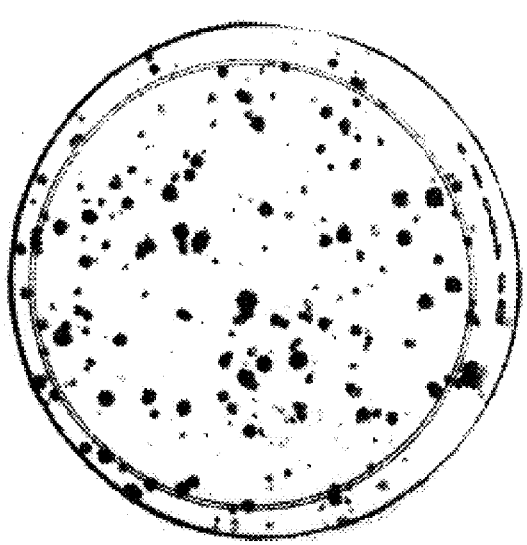
H62.B3
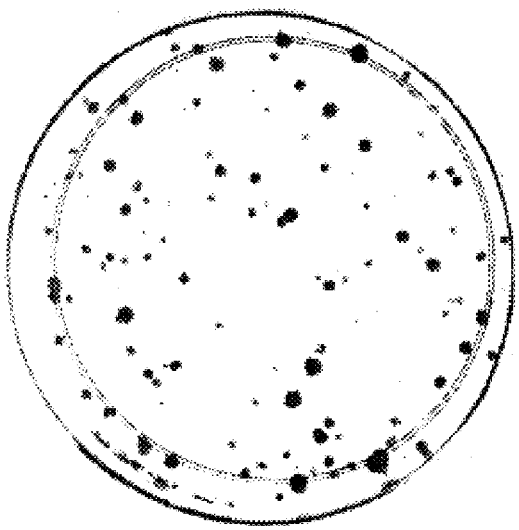
H62.B5
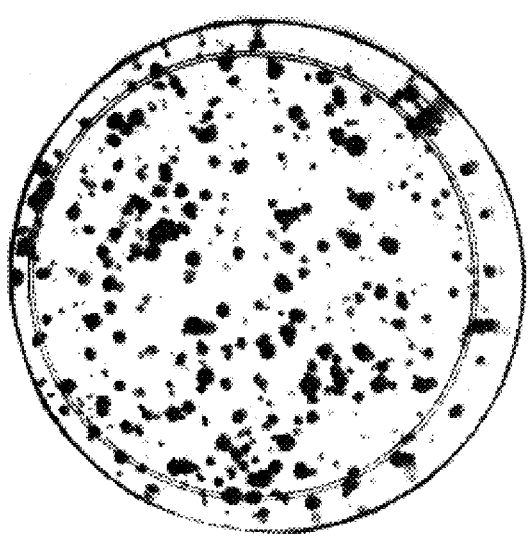

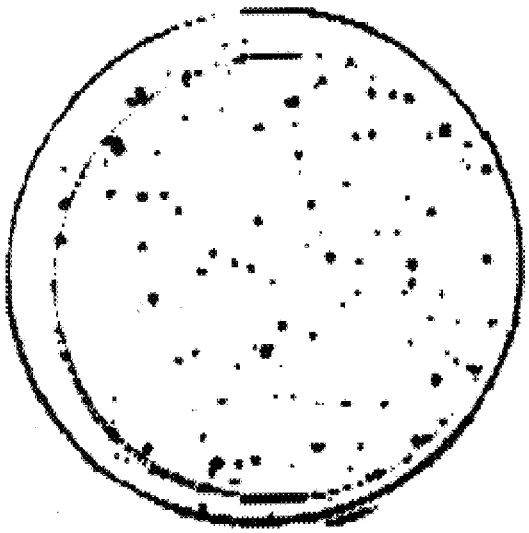
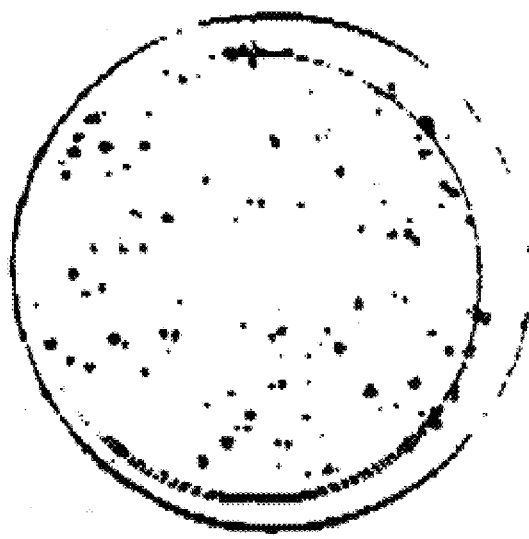
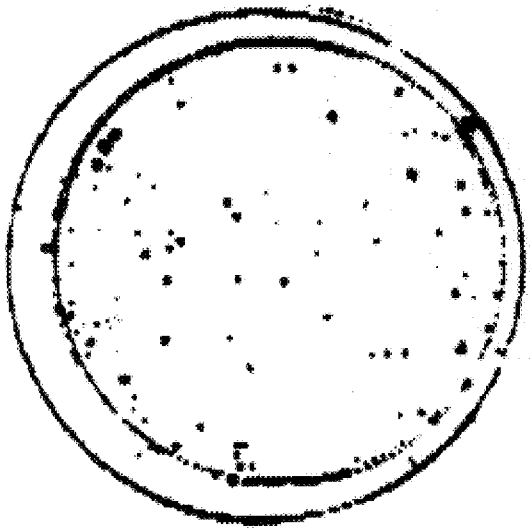
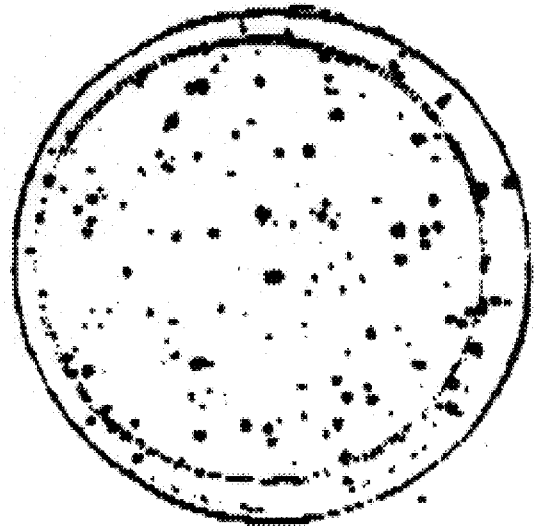
Figure 5G

Figure 6

| | | | | |
|---|---|---|---|---|
| AACTGGGGTC | CCTTGGGGCG | CCCCACGCTG | CTTCCACACA | CACCACCTCT | GGCCTTGGGT | 60
| GGTGGCATTA | CAGGGATGAG | GGAGTCACTG | TGGGTGGCCA | CAGGGCTATG | GCCAAGCGTT | 120
| CCCTGGCCGT | CTTCCTCTGG | CCTCAGCTTT | GTTCCTATAG | GCTGCCCGCG | CCGTGGGCTG | 180
| CAGGTCTCGC | CGCCCGCTTG | ATCCCTGAGG | TGTTTCCATG | CTGCGGGTGG | TGCTTCC | 237

```
ATACACACAA ATTTACACAT GCAAACATGC ATGCACTGGG AAAAGATCTG CCCAATGTA    60
TTAAACCATT TATGTTTCAG CCACAAAATT TCCTAGTCTG TCACAGCTCT GGAGTCACCA  120
GAACCCTATC ATTTCACCAA CCCCACAGGG GCAAGCAACA TCTAGGAATC TGATTTTAAT  180
CAGAGTTTCT TGATCTTCAT CTGTTTGC                                     208

```
GTGGAGTCCT GGGTGGAGGA TGGTCATTAC AAAGAGCAAG CCATCATTAC AACTTACAAG   60
CCCAACCCT  TGTGTGCTCT GGGAGGTTA  GAAGAGCTGG AGATTGAGTT AATAATCATG  120
CATGCCTGAG AAATGAAGCT CCATTTTGAA AAACCCCTAA AAGACAAAGT TTAGAGAGCT  180
ACTAGATTGG TGAACACATC TACGAGCTAT GAGGGTTGCT G                      221
```

```
GGCATAGAGT CCTGTTGGTT TTTTCTTCAC AAATGTTTTA TTTATCTGCT TTCATCACTA    60
ATCCCAATCT AGACTTCTTC ATGCCTGCTC ATTGCAAAAG CTCATCAGCT ATATTTTGCT   120
GATTCTAGAT TTTTTCCTTA TAATCTCTCC AGCAGAGCTG ACAACATAAT CTTGTTTAGT   180
TGCCACTTTG ACCACATTAT TCCTGCCCAA AATACCTTCA GTGACTTCCG TCTTCAGATC   240
AAATTCTTT                                                          249

```
GCAGCTCCCT  TGAACATGGA  GGCCCCAGCG  AGATGAGACC  CCCACGAGAG  GACTCTCGAC   60
CTCTACCCTG  GTTACACATG  CTTCTCATCC  GCTCTCCAGC  TTGGCGTGGA  GCTCAGCAGC  120
AGGGAGCAGG  TGTGAGGTGA  GGTGCCACGC  CTTGAGAAAC  CCCAGGAATC  GGCACACTGT  180
TCTCACGTAG  CAGCCAGAGT                                                  200
```

```
TCAGAATACA  GTGATGAAAA  TTCATTTTGA  AACTCAAATA  TTTTATTTTG  GATATTCTCC   60
TGTTTTTATT  AAACCAGTGA  TTACACCTGG  CCATCCCTCT  AAATGTTCTA  GGAAGGCATG  120
TCTATTGTGA  TTTTGATGAA  GACAGAATTA  TTTTTCTCTG  TAGAAACACA  GATACCACTT  180
TATC                                                                   184

```
GAATAATTGC AGGCCTGCGA CAGAGCTTGG CAGTGAGACA ACATTGCAAG CCGGGATACT    60
GCAACTCCCA ATACACTCCC TTCTTTGCTT GTTTTATACT CAATGTATGC CGGTTCTGTC   120
CCAGCAGGTG AGATGTGTGG CTGCCAGTCT TTCGGTGGCT TTGAAAGGTA CTTGGAAT     178
```

```
CTGAGGCCTG CCTGGGACCT GGAGACCTCC TGGGGTCAAT CTATCCACCT TGGGCCTTAT    60
GACCAATTGG GGCTTAAGGA TCTACTTAGA GACTGGTGTC AACCTGGAAC CTGGAACCTG   120
ATGTCCACTT GGAGTCTGGT GTACACCTTG GGCCTGATGC CCACCTTGGC ACAGGTGTAC   180
```

| | | | | | |
|---|---|---|---|---|---|
|AGCCCTTTCA|GTAACTATCA|GGAGCCCTGA|AACGGTAGAG|GCACTGCCAT|CCTTGTGGA 60|
|TACTCAAAGC|CCACAGGGCT|TTTCCCTCCC|TATTGCATCT|TCTGATGCTC|CCCACACCCA 120|
|CCCTCCACCT|CTCCACCTCT|GTGGTGTTCC|CATTTGTGTG|TTTCCCATCT|GTGGAGCCAG 180|
|ACTGTTTGAG|CAATAGCTTA|GCAGCGGAGTC|AG| | 212|

```
GGCAAGTTAT TTAGGAATGA GGAGGTGACA GCTGTAACTC AGTGTGGTTT TGCAGCTGCC    60
TACGTTAGTA CCAGGTATTC CATAAAACTC TGCAGAGGTC ATTTACATTT CGTAAATTCT   120
GT                                                                 122

```
CCCCGAGGAG  AAGGCACCGA  GCCCAGACGA  TCCCGAGCTG  GCCCAGAGGA  GCTGGGGAAG   60
ATCCTTCAGG  GTGTGGTAGT  GGTGCTGAGT  GGCTTCCAGA  ACCCCTTCCA  CTCCGAGCTG  120
CGAGATAAGG  CCCTAGAGCT  TGGGGCCAAG  TATCGGCCAG  ACTGGACCCG  GGACAGCACG  180
CACCTCATCT  GTGCCTTTGC  C                                              201
```

```
GCCAGGAGGA GCGCGCGGCA CAGGGTGCCG CTGACCGAGG CGTGCAAAGA CTCCAGAATT   60
GGAGGCATGA TGAAGACTCT GCTGCTGTTT GTGGGGCTGC CGCTGACCTG GGAGAGTGGG  120
CAGGTCCTGG GGACCAGAC  GGTCTCAGAC AATGAGCTCC AGGAAATGTC CAATCAGGGA  180
AGTAAGTACG TCAAT                                                   195
```

```
CAGCTACCCT CCTGTGAGAG TCTGAAGGAT ACTATTGCCA GAGCTCTGCC CTTCTGAAT    60
GAAGAAATAG TTCCCCAGAT CAAGGAGGGG AAACGTGTAC TGATTGCAGC CCATGGCAAC  120
AGCCTCCGGG GCATTGTCAA GCATCTGGAG GGTCTCTCTG AAGAGGCTAT CATGGAGCTG  180
AACCTGCC                                                           188
```

```
CCTCTCATGA  TCCAGCCACA  AAGGCTTGCC  TGAGTCCTTG  GGAAGGTTCC  AGATCAGGCT   60
TCCCGTCAGA  CGCTGTCCTC  ACCTCCGATG  ATCTGCTCCA  ATGGCATCTG  TGACTCCGCC  120
AAAGCCCTGC  TCTTTCAGAA  GGGTCTCCAG  TTCCCGGCTG  ACTTTGCCCA  CAACGGGTGG  180
CCCCCAGAAG  GTGAGGGCCG  TGTACAGCTG  TACCAGGGAG  GCCCCTGCCC  GGATCTTC    238

```
HL6.10   CCCCGAGGAGAAGGCACCGAGCCCAGACGATCCCGAGCTGGCCCAGAGAGCTGGGGAAG    60
         ************************ ***********************************
XRCC1    CCCGAGGAGAAGGCACCGAGCCCAGACGACCCCGAGCTGGCCCAGAGAGCTGGGGAAG  1502

HL6.10   ATCCTTCAGGGTGTGGTAGTGGTCTGAGTGGCTTCCAGAACCCCTTCCACTCCGAGCTG   120
         ********************************************* * ***********
XRCC1    ATCCTTCAGGGTGTGGTAGTGGTCTGAGTGGCTTCCAGAACCCCTTCCGCTCCGAGCTG  1562

HL6.10   CGAGATAAGGCCCTAGAGCTTGGGGGCCAAGTATCGGCCAGACTGACCCGGGACAGCACG   180
         *********************************************************
XRCC1    CGAGATAAGGCCCTAGAGCTTGGGGGCCAAGTATCGGCCAGACTGACCCGGGACAGCACG  1622

HL6.10   CACCTCATCTGTGCCCTTTGCC                                         201
         **********************
XRCC1    CACCTCATCTGTGCCCTTTGCC                                        1643
```

Figure 21

```
HL7.1    GCCAGGAGGAGCGGGCGGGCACAGGGTGCCCGCTGACCGAGGCGTGCAAAGACTCCAGAATT    60
              *****                ************************************
TRPM-2                       CGCGG-ACAGGGTGCCCGCTGACCGAGGCGTGCAAAGACTCCAGAATT    46

HL7.1    GGAGGCATGATGAAGACTCTGCTGTTGTGGGGCTGCCGCTGACCTGGGAGAGTGGG        120
         ******************************            ******************
TRPM-2   GGAGGCATGATGAAGACTCTGCTGTTGTGGGGCTGCTGCTGACCTGGGAGAGTGGG        106

HL7.1    CAGGTCCTGGGGACCAGACGGTCTCAGACAATGAGCTCCAGAAATGTCCAATCAGGA        180
         ***************************************+******************
TRPM-2   CAGGTCCTGGGGGACCAGACGGTCTCAGACAATGAGCTCCAGAAATGTCCAATCAGGA      166

HL7.1    AGTAAGTACGTCAAT        195
         ***************
TRPM-2   AGTAAGTACGTCAAT        181
```

Figure 22

```
HL7.10    CAGCTACCCCTCCTCTGTGAGAGTCTGAAGGATACTATTGCCAGAGCTCTGCCCTTCTGAAT    60
          ************************************************************
PGAM-B    CAGCTACCCCTCCTCTGTGAGAGTCTGAAGGATACTATTGCCAGAGCTCTGCCCTTCTGAAT   535

HL7.10    GAAGAAATAGTTCCCCAGATCAAGGAGGGGAAACGTGTACTGATTGCAGCCCATGGCAAC    120
          ************************************************************
PGAM-B    GAAGAAATAGTTCCCCAGATCAAGGAGGGGAAACGTGTACTGATTGCAGCCCATGGCAAC    595

HL7.10    AGCCTCCGGGGCATTGTCAAGCATCTCGAGGGTCTCTCTGAAGAGGCTATCATGGAGCTG    180
          ************************************************************
PGAM-B    AGCCTCCGGGGCATTGTCAAGCATCTCGAGGGTCTCTCTGAAGAGGCTATCATGGAGCTG    655

HL7.10    AACCTGCC    188
          ********
PGAM-B    AACCTGCC    663
```

Figure 23

```
HL7.11    CCTCTCATGATCCAGCCACAAAGGCTTGCCTGAGTCCTTGGGAAGGTTCCAGATCAGGCT    60
          ************************************************************
DIHYODH   CCTCTCATGATCCAGCCACAAAGGCTTGCCTGAGTCCTTGGGAAGGTTCCAGATCAGGCT    1210

HL7.11    TCCGTCAGACGCTGTCTCCACCTCCGATGATCTGCTCCAATGGCATCTGTGACTCCGCC    120
          ************************************************************
DIHYODH   TCCGTCAGACGCTGTCTCCACCTCCGATGATCTGCTCCAATGGCATCTGTGACTCCGCC    1150

HL7.11    AAAGCCCTGCTCTTTCAGAAGGGTCTCCAGTTCCCGCTTGCCCACAACGGGTGG    180
          ************************************   *********************
DIHYODH   AAAGCCCTGCTCTTTCAGAAGGGCCTCCAGTTCCCGCTTGCCCACAACGGGTGG    1090

HL7.11    CCCCAGAAGGTGAGGGCCCGTGTACAGCTGTACCAGGGAGGCCCTGCCCGGATCTTC    238
          *************   ********************************************
DIHYODH   CCCCAGAAGGGTAGGGCCCGTGTACAGCTGCACCAGGGAGGAGGCCCTGCCCGGATCTTC    1032
```

Figure 24

| | | | | | |
|---|---|---|---|---|---|
| H91.E4 | CAACAACAAA | AACAGTCTCG | TAAGCCCAGC | CCAAGAGCCC | GTGCCCTTGC | 139 |
| CaMK γB | CAACAACAAA | AACAGTCTCG | TAAGCCCAGC | CCAAGAGCCC | GCCCCCTTGC | 1048 |
| H91.E4 | AGACGGCCAT | GGAGCCACAA | ACCACTGTGG | TACACAACGC | TACAGATGGG | 89 |
| CaMK γB | AGACGGCCAT | GGAGCCACAA | ACCACTGTGG | TACACAACGC | TACAGATGGG | 1098 |
| H91.E4 | ATCAAGGGCT | CCACAGAGAG | CTGCAACACC | ACCACAGAAG | ATGAGGACCT | 39 |
| CaMK γB | ATCAAGGGCT | CCACAGAGAG | CTGCAACACC | ACCACAGAAG | ATGAGGACCT | 1148 |
| H91.E4 | CAAAGTGCGA | AAACAGGAGA | TCATTAAGAT | TACAGAAC | | 1 |
| CaMK γB | CAAAGTGCGA | AAACAGGAGA | TCATTAAGAT | TACAGAAC | | 1186 |

Figure 25

```
H62.B2     ACAGAATTTA CGAAATGTAA ATGACCTCTG CAGAGTTTTA TGGAATACCT    73
           ********** ********** ********** ********** **********
PG40 core  ACAGAATTTA CGAAATGTAA ATGACCTCTA CAGAGTTTTA TGGAATACCT  1345

H62.B2     GGTACTAACG TAGGCAGCTG CAAAACCACA CTGAGTTACA GCTGTCA--C    25
           ********** ********** ********** ********** *******  *
PG40 core  GGTACTAACG TAGGCAGCTG CAAAACCACA CTGAGTTACA GCTGTCAGCC  1395

H62.B2     CTCCTCATTC CTAAATAACT TGCC                                  1
           ********** ********** ****
PG40 core  CTCCTCATTC CTAAATAACT TGCC                               1419
```

GENES AND GENETIC ELEMENTS ASSOCIATED WITH SENSITIVITY TO CISPLATIN

This application is a continuation of application Ser. No. 08/199,900, filed Feb. 22, 1994, abandoned, which is a continuation-in-part of U.S. patent application Ser. No. 08/033,086, filed Mar. 9, 1993, now abandoned, which in turn is a continuation-in-part of U.S. patent application Ser. No. 07/599,730 filed Oct. 19, 1990, now U.S. Pat. No. 5,217,889, which is a continuation-in-part of said application Ser. No. 08/199,900, which is also a continuation-in-part of U.S. patent application Ser. No. 08/039,385 filed as PCT/US91/07492 Oct. 11, 1991, now U.S. Pat. No. 5,811,234 which is a continuation-in-part of U.S. Ser. No. 07/599,730, filed on Oct. 19, 1990, now U.S. Pat. No. 5,217,889, issued Jun. 8, 1993. +gi This invention was made with government support under grants CA-56737 by the National Institutes of Health. The government has certain rights in the invention.

BACKGROUND OF THE INVENTION

1. Field of the Invention

The invention relates to genetic factors associated with sensitivity to chemotherapeutic drugs. More particularly, the invention relates to methods for identifying such factors as well as to uses for such factors. The invention specifically provides genetic suppressor elements derived from genes associated with sensitivity of mammalian cells to platinum-based chemotherapeutic drugs, such as cisplatin, and therapeutic and diagnostic uses related thereto.

2. Summary of the Related Art

A broad variety of chemotherapeutic agents are used in the treatment of human cancer. For example the textbook CANCER: Principles & Practice of Oncology, 2d Edition, (De Vita et al., eds.), J. B. Lippincott Company, Philadelphia, Pa. (1985) discloses as major antineoplastic agents the plant alkaloids vincristine, vinblastine, and vindesine; the antibiotics actinomycin-D, doxorubicin, daunorubicin, mithramycin, mitomycin C and bleomycin; the antimetabolites methotrexate, 5-fluorouracil, 5-fluorodeoxyuridine, 6-mercaptopurine, 6-thioguanine, cytosine arabinoside, 5-aza-cytidine and hydroxyurea; the alkylating agents cyclophosphamide, melphalan, busulfan, CCNU, MeCCNU, BCNU, streptozotocin, chlorambucil, bis-diaminedichloroplatinum, azetidinylbenzoquinone; and the miscellaneous agents dacarbazine, mAMSA and mitoxantrone.

Chemotherapeutic agents have proven to be very useful in the treatment of cancer. Unfortunately, some tumor cells become resistant to specific chemotherapeutic agents, in some instances even to multiple chemotherapeutic agents. Such drug resistance or multiple drug resistance can theoretically arise from either the presence of genetic factors that confer resistance to the drugs, or from the absence of genetic factors that confer sensitivity to the drugs. The former type of factors have been identified, and include the multiple drug resistance gene mdr-1 (see Chen et al., 1986, Cell 47: 381–389). However, the latter type of factor remains largely unknown, perhaps in part because the absence of such factors would tend to be a recessive trait.

The platinum coordination complexes, typified by cisplatin (cis-diamminedichloroplatinum (II)) (Reed, 1993, in Cancer, Principles and Practice of Oncology, ibid., pp. 390–4001), have been described as "the most important group of agents now in use for cancer treatment". These agents, used as a part of combination chemotherapy regimens, have been shown to be curative for testicular and ovarian cancers and beneficial for the treatment of lung, bladder and head and neck cancers. DNA damage is believed to be the major determinant of cisplatin cytotoxicity, though this drug also induces other types of cellular damage.

In addition to cisplatin, this group of drugs includes carboplatin, which like cisplatin is used clinically, and other platinum-containing drugs that are under development. These compounds are believed to act by the same or very similar mechanisms, so that conclusions drawn from the study of the bases of cisplatin sensitivity and resistance are expected to be valid for other platinum-containing drugs.

Cisplatin is known to form adducts with DNA and to induce interstrand crosslinks. Adduct formation, through an as yet unknown signalling mechanism, is believed to activate some presently unknown cellular enzymes involved in programmed cell death (apoptosis), the process which is believed to be ultimately responsible for cisplatin cytotoxicity (see Eastman, 1990, Cancer Cells 2: 275–2802).

Many current attempts to optimize the clinical efficacy of platinum compounds are directed at mechanisms that determine cellular sensitivity or resistance to these drugs. Selection of cisplatin-resistant mutant cell lines has revealed several potential mechanisms of cisplatin resistance, none of which have yet been unambiguously proven by molecular genetic analysis (reviewed in Reed, 1993, ibid.).

The first such mechanism involves decreased cellular accumulation of the drug. Observed changes in cisplatin transport in different cell lines may be related to the altered expression of specific membrane proteins. One example of such a protein is a protein termed SQML that is decreased in some cisplatin-resistant cell lines (Bemal et al., 1990, Mol. Cell. Biochem. 95: 61–703). Another such protein is a 200 kilodalton (kDa) glycoprotein which expression has been found to be increased in another such cell line having diminished intracellular accumulation of cisplatin (Kawai et al., 1990, J. Biol. Chem. 265: 13137–13142). Interestingly, a resistance-associated defect in cisplatin uptake has been reported to be a recessive genetic trait, i.e., the phenotype of decreased cisplatin uptake is associated with a loss of gene function (Richon et al., 1987, Cancer Res. 47: 2056–2061).

Another possible mechanism for cisplatin resistance is cytosolic inactivation (termed "quenching") of the drug by sulfhydryl-containing proteins or glutathione. For example, some cisplatin-resistant cell lines have been found to exhibit increased expression of the sulfhydryl-containing proteins, the metallothioneins (Reed, ibid.). Increased levels of glutathione or increased rates of glutathione synthesis have also been correlated with cisplatin resistance (Reed, ibid.). Although it has been reported that transfection of a metallothionein gene into a cell induces cisplatin resistance in such cells (Kelley et al., 1988, Science 241: 1813–1815), these observations have not been confirmed by others (Schilder et al., 1990, Int. J. Cancer 45: 416–422). In another report (Miyazaki et al., 1990, Biochem. Biophys. Res. Commun. 166: 1358–1364) that has not been successfully reproduced by others (Nakagawa et al., 1990, J. Biol. Chem. 265: 4296–4301), cisplatin resistance in cells transfected with the human glutathione-S-transferase (GST)-π gene was correlated with GST-π expression. Furthermore, transfection of cDNAs encoding GSTs of the μ and α classes also has been reported to have had no effect on cisplatin resistance in recipient cells (Leyland-Jones et al., 1991, Cancer Res. 51: 587–594; Townsend et al., 1992, Mol. Pharmiacol. 41: 230–236).

Yet another proposed mechanism to explain cisplatin resistance involves increased repair of DNA adducts. Treatment of cells with non-specific agents that inhibit DNA repair has been reported to sensitize such cells to cisplatin; conversely, increased rates of repair have been observed in some cisplatin-resistant cell lines (Reed, ibid.). It is possible that cisplatin-induced DNA lesions may be repaired by a specialized enzymatic system. Several DNA-binding proteins have been shown to selectively bind to cisplatin-damaged DNA, suggesting that they may be involved in damage repair (Chu & Chang, 1990, Proc. Natl Acad. Sci. USA 87: 3324–3328; Chao et al., 1991, Mol. Cell. Biol. 11: 2075–2080; Bruhn et al., 1992, Proc. Natl. Acad. Sci. USA 89: 2307–2311); however, other functions for these proteins are also conceivable. It has also been reported that transfer of a human DNA repair gene (ERCC-1) to repair-deficient CHO cells led to increased resistance to cisplatin (Reed et al., 1989, Proc. Amer. Assoc. Cancer Res. 30: 488). Paradoxically, when wild-type CHO cells were transfected with the same gene, their cisplatin resistance was reported to decrease rather than increase (Bramson & Panasci, 1993, Cancer Res. 53: 3237–3240), casting doubt on the significance of the earlier observation.

It has also been suggested that pleiotropic regulatory changes induced by the oncogenes H-ras (Sklar, 1988, Cancer Res. 48: 793–797; Isonishi et al., 1991, Cancer Res. 51: 5903–5909; Peters et al., 1993, Int. J. Cancer 54: 450–455), myc (Niimi et al., 1991, Br. J. Cancer 63: 237–241), trk (Peters et al., 1993, ibid.) and fos (Scanlon et al., 1991, Proc. Natl. Acad. Sci. USA 88: 10591–10595) lead to increased cisplatin resistance. Studies with a ribozyme that targets c-fos has suggested that inhibition of c-fos expression may be correlated with cell sensitization to cisplatin (Scanlon et al., ibid.). The association of H-ras with cisplatin resistance, on the other hand, has been called into question by the results of a recent gene transfer study (Perez et al., 1993, Cancer Res. 53: 3771–3775).

Thus, the available evidence suggests the existence of multiple biochemical and physiological mechanisms that are involved in determining cellular sensitivity or resistance to cisplatin. Although several candidate genes responsible for these mechanisms have been suggested, what role, if any, these genes play in cisplatin resistance has not been unambiguously established at the present time.

The unambiguous identification of genes associated with cisplatin sensitivity is thus desirable, because the discovery of such genes can lead to both diagnostic and therapeutic approaches for cancer cells and for drug resistant cancer cells, as well as to improvements in gene therapy and rational drug design. Recently, some developments have been made in the difficult area of isolating recessive genes, including those involved in cytotoxic drug sensitivity. Roninson et al., U.S. Pat. No. 5,217,889 (issued Jun. 8, 1993) teach a generalized method for obtaining genetic suppressor elements (GSEs), which are dominant negative factors that confer the recessive-type phenotype for the gene to which the particular GSE corresponds. (See also Holzmayer et al., 1992, Nucleic Acids Res. 20: 711–717). Gudkov et al., 1993, Proc. Natl. Acad. Sci. USA 90: 3231–3235 teach isolation of GSEs from topoisomerase II cDNA that induce resistance to topoisomerase II-interactive drugs. Abandoned U.S. patent applications Ser. No. 08/033,086, filed Mar. 3, 1993, and Ser. No. 08/177,571, filed Jan. 5, 1994, disclosed the discovery by the present inventors of the novel and unexpected result that GSEs isolated from RNA of cells resistant to the anticancer DNA damaging agent, etoposide, include a GSE encoding an antisense RNA homologous to a portion of a kinesin heavy chain gene. Additionally, abandoned U.S. patent application Ser. No. 08/033,086 disclosed two other GSEs from previously-unknown genes, the expression of said GSEs conferring etoposide resistance on mammalian cells. These results further underscored the power of the GSE technology developed by these inventors to elucidate unexpected mechanisms of drug resistance in cancer cells, thereby providing the opportunity and the means for overcoming drug resistance in cancer patients. This technology has now been applied to isolating and identifying GSEs that confer resistance to cisplatin in cells expressing such GSEs, and for isolating and identifying genes associated with sensitivity of human tumor cells to cisplatin.

BRIEF SUMMARY OF THE INVENTION

The invention provides genetic suppressor elements (GSEs) that are random fragments derived from genes associated with sensitivity to platinum-based drugs, particularly cisplatin, and that confer resistance to platinum-based drugs upon cells expressing such GSEs. The invention is based in part on the discoveries disclosed in abandoned U.S. patent applications, Ser. No. 08/033,086, filed Mar. 3, 1993 and Ser. No. 08/177,571, filed Jan. 5, 1994, now abandoned both incorporated by reference, providing a method for identifying and isolating GSEs that confer resistance to any chemotherapeutic drug for which resistance is possible.

In a first aspect, the invention provides a method for identifying GSEs that confer resistance to platinum-based drugs, including cisplatin. This method utilizes cisplatin selection of cells that harbor clones from a random fragment expression library derived from total cDNA derived from cisplatin-sensitive cells, and subsequent rescue of library inserts from drug-resistant cells. In a second aspect, the invention provides a method for identifying and cloning genes that are associated with sensitivity to cisplatin, and also provides the genes themselves. This method comprises the steps of screening a full length cDNA library with a GSE that confers upon cells resistance to cisplatin (or, alternatively, with an oligonucleotide or polynucleotide constituting a portion of such a GSE) and determining the nucleotide sequence of the cDNA insert of any positive clones obtained. Alternatively, the technique of "anchored PCR" (see Example 5 below) can be used to isolate cDNAs corresponding to cisplatin resistance-conferring GSEs. Also embodied in this aspect of the invention is isolation of genomic DNA encoding genes associated with sensitivity to platinum-based drugs, for example from genomic libraries. In a third aspect, the invention provides a method for obtaining GSEs having optimized suppressor activity for a gene associated with sensitivity to platinum-based drugs. This method utilizes drug selection of cells that harbor clones from a random fragment expression library derived from DNA of a gene associated with sensitivity to a platinum-based drug such as cisplatin, and subsequent rescue of the library inserts from drug resistant cells. In a fourth aspect, the invention provides synthetic peptides and oligonucleotides that confer upon cells resistance to, for example, cisplatin. These synthetic peptides and oligonucleotides are designed based upon the sequence of drug-resistance conferring GSEs according to the invention.

In a fifth aspect, the invention provides a diagnostic assay for tumor cells that are resistant to platinum-based drugs due to the absence of expression or underexpression of a particular gene. This diagnostic assay comprises quantitating the level of expression of the particular gene product by a particular tumor cell sample to be tested. One feature of this aspect of the invention is the development of antibodies specific for proteins whose underexpression or absence of expression is associated with such resistance to platinum-based drugs. Such antibodies have utility as diagnostic agents for detecting cisplatin resistant tumor cells in tumor samples. In a sixth aspect, the invention provides dominant selectable markers that are useful in gene co-transfer studies. These dominant selectable markers are drug resistance-conferring GSEs according to the invention operably linked to appropriate transcriptional control elements. In a seventh aspect, the invention provides in vivo selectable markers that are useful both for gene therapy and for enhanced chemotherapy for cancer. Such in vivo selectable markers are transferred, for example, into blood progenitor cells, which are then used to repopulate the patient's blood exclusively with cells that contain a co-transferred therapeutic gene, or, for chemotherapeutic purposes, just the resistance-conferring GSE. In an eighth aspect, the invention provides a starting point for in vitro drug screening and rational design of pharmaceutical products that are useful against tumor cells that are resistant to cisplatin and other platinum-based drugs. By examining the structure, function, localization and pattern of expression of genes associated with sensitivity to cisplatin, strategies can be developed for creating pharmaceutical products that will overcome drug resistance in tumor cells in which such genes are either not expressed or underexpressed.

Also provided by the invention are cultures of mammalian cells which express the cisplatin resistance-conferring GSEs of the invention and are cisplatin resistant thereby. Such cells are useful for determining the physiological and biochemical basis for cisplatin toxicity and resistance in tumor cells. Such cells also have utility in the development of pharmaceutical and chemotherapeutic agents for overcoming such resistance, and thus are ultimately useful in establishing improved chemotherapeutic protocols to more effectively treat neoplastic disease.

Specific preferred embodiments of the present invention will become evident from the following more detailed description of certain preferred embodiments and the claims.

BRIEF DESCRIPTION OF THE DRAWINGS

FIGS. 4A and 4B shows polyacrylamide gel electrophoretic analysis of PCR fragments enriched by selection for cisplatin resistance-conferring GSEs.

FIGS. 5A through 5G shows resistance to various concentrations of cisplatin, conferred upon cells by the GSEs HL7.1, HL7.2, HL7.4 (FIG. 5A), HL7.10, HL7.11, and HL7.12 (FIG. 5B) HL6.1, HL6.10 (FIG. 5C), H63.C8, HL4.1 (FIG. 5D), H91.E2, H91.E2, H93.G6 (FIG. 5E), H62.B2, H62.B3, H62.B5 (FIG. 5F). Clones that scored as inactive in this assay are exemplified by the elements H62.B3 (FIG. 5F) and H63.C7, HL4.4 and HL6.4 (FIG. 5G).

FIG. 6 shows the nucleotide sequence of the GSE H62.B5 (SEQ ID NO:3).

FIG. 7 shows the nucleotide sequence of the GSE H63.C8 (SEQ ID NO:4).

FIG. 8 shows the nucleotide sequence of the GSE H91.E2 (SEQ ID NO:5).

FIG. 9 shows the nucleotide sequence of the GSE H93.G6 (SEQ ID NO:6).

FIG. 10 shows the nucleotide sequence of the GSE HL4.1 (SEQ ID NO:7).

FIG. 11 shows the nucleotide sequence of the GSE HL6.1 (SEQ ID NO:8).

FIG. 12 shows the nucleotide sequence of the GSE HL7.2 (SEQ ID NO:9).

FIG. 13 shows the nucleotide sequence of the GSE HL7.4 (SEQ ID NO:10).

FIG. 14 shows the nucleotide sequence of the GSE HL7.12 (SEQ ID NO:11).

FIG. 15 shows the nucleotide sequence of the GSE H62.B2 (SEQ ID NO:12).

FIG. 16 shows the nucleotide sequence of the GSE HL6.10 (SEQ ID NO:13).

FIG. 17 shows the nucleotide sequence of the GSE HL7.1 (SEQ ID NO:14).

FIG. 18 shows the nucleotide sequence of the GSE HL7.10 (SEQ ID NO:15).

FIG. 19 shows the nucleotide sequence of the GSE HL7.11 (SEQ ID NO:16).

FIG. 20 shows a comparison between the nucleotide sequence of GSE HL6.10 (SEQ ID NO:13) and the XRCC1 gene sequence (SEQ ID NO:17).

FIG. 21 shows a comparison between the nucleotide sequence of GSE HL7.1 (SEQ ID NO:14) and the TRPM2 gene sequence (SEQ ID NO:18).

FIG. 22 shows a comparison between the nucleotide sequence of GSE HL7.10 (SEQ ID NO:15) and the PGAM-B gene sequence (SEQ ID NO:19).

FIG. 23 shows a comparison between the nucleotide sequence complementary to that of GSE HL7.11 (SEQ ID NO:15) and the DHOD gene sequence (SEQ ID NO:20).

FIG. 24 shows a comparison between the nucleotide sequence compementary to that of GSE H91.E2 (SEQ ID NO:17) and the CaMKGB gene sequence (SEQ ID NO:21).

FIG. 25 shows a comparison between the nucleotide sequence complementary to that of GSE H62.B2 (SEQ ID NO:12) and the decorin gene sequence (SEQ ID NO:22).

DETAILED DESCRIPTION OF THE PREFERRED EMBODIMENTS

Figure 1:
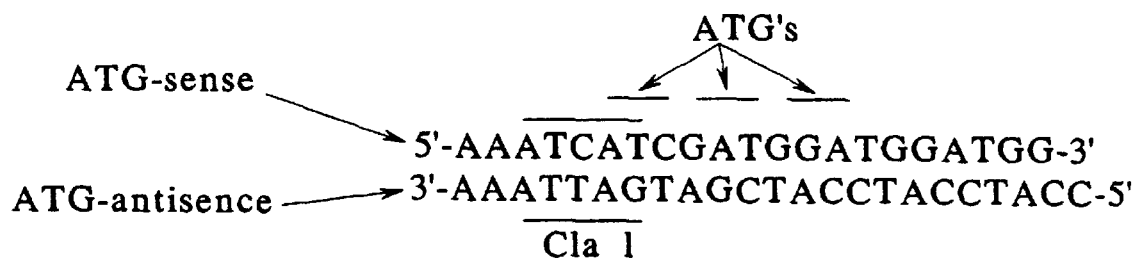
FIG. 1 shows the structure of the adaptor used in cDNA cloning. The nucleotide sequences are shown for the ATG-sense (SEQ ID No:1) and ATG-antisense (SEQ ID NO:2) strands of the adaptor.

The invention relates to means for suppressing specific gene functions that are associated with sensitivity to platinum-based drugs, including cisplatin. The invention provides genetic suppressor elements (GSEs) that have such suppressive effect and thus confer resistance to cisplatin on cells expressing such GSEs. The invention further provides methods for identifying such GSEs, as well as methods for their use. For the purposes of this invention, the term "platinum-based drugs" is intended to encompass the clinically-approved platinum-based drugs, such as cisplatin and carboplatin, as well as any platinum-based drugs currently indevelopment or to be developed that act with the same or similar mechanism as cisplatin.

In a first aspect, the invention provides a method for identifying GSEs that confer resistance to cisplatin. The GSEs identified by this method will be homologous to a gene that is associated with sensitivity to cisplatin. For purposes of the invention, the term "homologous to a gene"

has two different meanings, depending on whether the GSE acts through an antisense or antigene mechanism, or through a mechanism of interference at the protein level. In the former case, a GSE that is an antisense or antigene oligonucleotide or polynucleotide is homologous to a gene if it has a nucleotide sequence that hybridizes under physiological conditions to the gene or its mRNA transcript by Hoogsteen or Watson-Crick base-pairing. In the latter case, a GSE that interferes with a protein molecule is homologous to the gene encoding that protein molecule if it has an amino acid sequence that is the same as that encoded by a portion of the gene encoding the protein, or that would be the same, but for conservative amino acid substitutions. In either case, as a practical matter, whether the GSE is homologous to a gene is determined by assessing whether the GSE is capable of inhibiting or reducing the function of the gene.

The method according to this aspect of the invention comprises the step of screening a total cDNA or genomic DNA random fragment expression library phenotypically to identify clones that confer resistance to cisplatin. Preferably, the library of random fragments of total cDNA or genomic DNA is cloned into a retroviral expression vector. In this preferred embodiment, retrovirus particles containing the library are used to infect cells and the infected cells are tested for their ability to show increased survival in the presence of cisplatin relative to uninfected cells. Preferably, the inserts in the library will range from about 100 bp to about 700 bp and more preferably, from about 200 bp to about 500 bp. Most preferably, the random fragment library will be a normalized library containing roughly equal numbers of clones corresponding to each gene expressed in the cell type from which it was made, without regard for the level of expression of any gene. However, normalization of the library is unnecessary for the isolation of GSEs that are homologous to abundantly or moderately expressed genes. Once a clonal population of cells that are resistant to cisplatin has been isolated, the library clone encoding the GSE is rescued from the cells. At this stage, the insert of the expression library may be tested for its nucleotide sequence. Alternatively, and preferably, the rescued library clone may be further tested for its ability to confer resistance to cisplatin in additional transfection or infection and selection assays, prior to nucleotide sequence determination. Determination of the nucleotide sequence, of course, results in the identification of the GSE. This method is further illustrated in Examples 1–4.

In a second aspect, the invention provides a method for identifying and cloning genes that are associated with sensitivity to cisplatin, as well as the genes derived by this method. This is because GSEs, or portions thereof, can be used as probes to screen full length cDNA or genomic libraries to identify their gene of origin. In some cases, genes that are associated with sensitivity to chemotherapeutic drugs such as cisplatin will turn out to be quite surprising. For example, GSEs that abrogate cisplatin include GSEs derived from the following human genes: XRCC1 (X-ray repair cross-complementing-1); TRPM-2 (testosterone-repressed prostatic message-2; phosphoglycerate mutase, isozyme B, non-muscle isoform; dihydroorotate dehydrogenase; calcium/calmodulin-dependent protein kinase, isoform γB; and chondroitin/dermatan sulfate proteoglycan core protein (decorin), as well as nine GSEs from previously unidentified human genes. In addition, GSEs conferring resistance to cisplatin may be derived from genes involved in programmed cell death. The method according to this aspect of the invention therefore also provides valuable information about the genetic basis for senescence and programmed cell death. Of particular utility for this latter purpose are GSEs isolated as disclosed herein for the human TRPM-2 gene, which is known to be a common marker for programmed cell death (apoptosis) in different tissues (see Example 5 below). The method according to this aspect of the invention and its use for studying genes identified thereby and their cellular effects are further illustrated in Example 6.

In a third aspect, the invention provides a method for obtaining GSEs having optimized suppressor activity for a gene associated with sensitivity to cisplatin. In the method according to this aspect of the invention, an initial GSE is obtained by the method according to the first aspect of the invention. Then, the gene from which the GSE is derived is identified and cloned by the method according to the second aspect of the invention. This gene is then randomly fragmented and cloned into an expression vector, preferably a retroviral vector, to obtain a random fragment expression library derived exclusively from the gene of interest. This library is then transferred to and expressed in mammalian cells, which are selected in the presence of cisplatin. As a practical matter, such a library will contain a much greater variety of GSEs derived from the gene of interest than will a random fragment library prepared from total cDNA. Consequently, the likelihood of obtaining optimized GSEs, as determined by maximized cisplatin resistance, from the single gene random fragment library approach is greater than from a total cDNA or genomic library, as shown in greater detail in Example 6.

In a fourth aspect, the invention provides synthetic peptides and oligonucleotides that are capable of inhibiting the function of genes associated with sensitivity to cisplatin. Synthetic peptides according to the invention have amino acid sequences that correspond to amino acid sequences encoded by GSEs according to the invention. Synthetic oligonucleotides according to the invention have nucleotide sequences corresponding to the nucleotide sequences of GSEs according to the invention. Once a GSE is discovered and sequenced, and its orientation is determined, it is straightforward to prepare an oligonucleotide corresponding to the nucleotide sequence of the GSE (for antisense-oriented GSEs) or amino acid sequence encoded by the GSE (for sense-oriented GSEs). In certain embodiments, such synthetic peptides or oligonucleotides may have the complete sequence encoded by the GSE or may have only part of the sequence present in the GSE, respectively. In certain other embodiments, the peptide or oligonucleotide may have only a portion of the GSE-encoded or GSE sequence. In such latter embodiments, undue experimentation is avoided by the observation that many independent GSE clones corresponding to a particular gene will have the same 5' or 3' terminus, but generally not both. This suggests that many GSE's have one critical endpoint, from which a simple walking experiment will determine the minimum size of peptide or oligonucleotide necessary to inhibit gene function. For peptides, functional domains as small as 6–8 amino acids have been identified for immunoglobulin binding regions. Thus, peptides or peptide mimetics having these or larger dimensions can be prepared as GSEs. For antisense oligonucleotides, inhibition of gene function can be mediated by oligonucleotides having sufficient length to hybridize to their corresponding mRNA under physiological conditions. Generally, oligonucleotides having about 12 or more bases will fit this description. Preferably, such oligonucleotides will have from about 12 to about 100 nucleotides. As used herein, the term oligonucleotide includes modified oligonucleotides having nuclease-resistant internucleotide linkages, such as phosphorothioate, methylphosphonate, phosphorodithioate, phosphoramidate, phosphotriester, sulfone, siloxane, carbonate, carboxymethylester, acetamidate, carbamate, thioether, bridged phosphoramidate, bridged methylene phosphonate and bridged phosphorothioate internucleotide linkages. The synthesis of oligonucleotides containing these modified linkages is well known in the art. (See e.g., Uhlmann and Peyman, 1990, *Chemical Reviews* 90:543–584; Schneider and Banner, 1990, *Tetrahedron Letters* 31: 335). The term oligonucleotides also includes oligonucleotides having modified bases or modified ribose or deoxyribose sugars.

In a fifth aspect, the invention provides a diagnostic assay for tumor cells that are resistant to cisplatin due to absence of expression or underexpression of a particular gene. By using the methods according to the first and second aspects of the invention such a gene is identified and cloned. To determine whether absence of expression or underexpression of such a gene is a naturally occurring, and thus medically significant basis for chemotherapeutic drug resistance, human tumor cells are treated with cytotoxic quantities of cisplatin to select for spontaneous drug resistant mutants. These mutants are then assessed for their level of expression of the particular gene of interest. Absence of expression or significantly reduced expression would be indicative for drug resistance. Accordingly, such reduced or absent expression can be the basis for a diagnostic assay for tumor cell resistance to cisplatin. A first embodiment of a diagnostic assay according to this aspect of the invention utilizes an oligonucleotide or oligonucleotides that is/are homologous to the sequence of the gene for which expression is to be measured. In this embodiment, RNA is extracted from a tumor sample, and RNA specific for the gene of interest is quantitated by standard filter hybridization procedures, RNase protection assay, or by quantitative cDNA-PCR (see Noonan et al., 1990, *Proc. Natl. Acad. Sci. USA* 87: 7160–7164). In a second embodiment of a diagnostic assay according to this aspect of the invention, antibodies are raised against a synthetic peptide having an amino acid sequence that is identical to a portion of the protein that is encoded by the gene of interest. These antibodies are then used in a conventional quantitative immunoassay (e.g., RIA or immunohistochemical assays) to determine the amount of the gene product of interest present in a sample of proteins extracted from the tumor cells to be tested, or on the surface or at locations within the tumor cells to be tested.

In a sixth aspect, the invention provides dominant selectable markers that are useful in gene co-transfer studies. Since GSEs according to the invention confer resistance to cisplatin, the presence of a vector that expresses the GSE can readily be selected by growth of a vector-transfected cell in a concentration of cisplatin that would be cytotoxic in the absence of the GSE. GSEs according to the invention are particularly well suited as dominant selectable markers because their small size allows them to be easily incorporated along with a gene to be cotransferred even into viral vectors having limited packaging capacity.

In a seventh aspect, the invention provides in vivo-selectable markers that are useful both in gene therapy and in enhancing the effectiveness of chemotherapy. For gene therapy, GSEs according to the invention can be co-transferred on a vector into human blood progenitor cells from a patient along with a therapeutic gene that, when expressed, will alleviate a genetic disorder. The cells can be selected in vitro for resistance to cisplatin, thereby assuring successful transfer of the GSE, and by implication, of the therapeutic gene as well. The progenitor cells containing the GSE and therapeutic gene can then be returned to the patient's circulation. The cells containing the GSE and therapeutic gene can also be selected in vivo by administration of cisplatin (to which the GSE confers resistance) in a concentration that is cytotoxic to normal blood cells. In this way, those cells having the GSE and therapeutic gene will repopulate the patient's blood.

For enhancement of chemotherapy, a GSE according to the invention can be transferred alone or with another gene on an expression vector into blood progenitor cells taken from a cancer patient. The cells are then returned to the patient's circulation and allowed time to begin repopulating the blood. Alternatively, in vitro selection of the progenitor cells harboring the GSE is carried out before re-introduciton of the cells into the patient. After an appropriate period, aggressive chemotherapy with cisplatin or combination chemotherapy using cisplatin and other chemotherapeutic drugs, can be carried out using higher than ordinary concentrations of cisplatin (to which the GSE confers resistance), since toxic side effects to the immune system, for example, will be avoided due to GSE expression in those cells.

In either of these therapeutic contexts, it may be desirable to have the GSE expressed in the progenitor cells (and subsequently in the blood cells), only when its expression is beneficial, i.e., during in vivo selection or chemotherapy. To accomplish this, an inducible promoter can be used to express the GSE. Then, the appropriate inducing agent is added to the cells prior to and during in vitro selection or prior to and during in vivo selection or chemotherapy. As long as the inducing agent is not normally present in the human body, the GSE will not be expressed at any other time.

In an eighth aspect, the invention provides a starting point for in vitro drug screening and rational design of pharmaceutical products that can counteract resistance by tumor cells to cisplatin. In this regard, the invention provides cultures of mammalian cells which express the cisplatin resistance-conferring GSEs of the invention and are cisplatin resistant thereby. Included within this aspect of the invention are cell cultures that are representative of almost any tissue or cell type for which cisplatin is normally toxic. Such cells are useful for determining the physiological and biochemical basis for cisplatin toxicity and resistance in tumor cells, as well as for screening pharmaceutical and chemotherapeutic agents for overcoming cisplatin resistance. Identification of such agents would lead to the development of improved chemotherapeutic protocols to more effectively treat neoplastic disease.

The protein sequence encoded by genes from which the GSEs were derived can be deduced from the cDNA sequence, and the function of the corresponding proteins may be determined by searching for homology with known genes or by searching for known functional motives in the protein sequence. If these assays do not indicate the protein function, it can be deduced through the phenotypic effects of the GSEs suppressing the gene. Such effects can be investigated at the cellular level, by analyzing various growth-related, morphological, biochemical or antigenic changes associated with GSE expression. The GSE effects at the organism level can also be studied by introducing the corresponding GSEs as transgenes in transgenic animals (e.g. mice) and analyzing developmental abnormalities associated with GSE expression. Gene function can also be studied by expressing the full-length cDNA of the corresponding gene, rather than a GSE, from a strong promoter in cells or transgenic animals, and studying the changes associated with overexpression of the gene.

Full-length or partial cDNA sequences can also be used to direct protein synthesis in a convenient prokaryotic or eukaryotic expression system, and the produced proteins can be used as immunogens to obtain polyclonal or monoclonal antibodies. These antibodies can be used to investigate protein localization and as specific inhibitors of protein function, as well as for diagnostic purposes. In particular, antibodies raised against a synthetic peptide encoded by part of the complement of the sequence of the GSEs HL7.11, H91.E2 or H62.B2, or the corresponding region of the human dihydroorotate dehydrogenase gene, the calcium/calmodulin-dependent protein kinase gene or the decorin gene, respectively, should be particularly useful, as should antibodies raised against an amino acid sequence encoded by part of the GSEs HL6.10, HL7.1 or HL7.10, or proteins encoded by the X-ray repair cross-complementing-1 gene, the testosterone-repressed prostatic message-2 gene, or the phosphoglycerate mutase, isozyme B, non-muscle isoform gene, respectively (see Examples 3 and 4 and FIGS. 15–20).

Understanding the biochemical function of a gene involved in drug sensitivity is likely to suggest pharmaceutical means to stimulate or mimic the function of such a gene and thus augment the cytotoxic response to anticancer drugs. For example, if the gene encodes an enzyme producing a certain compound, such a compound can be synthesized chemically and administered in combination with cytotoxic drugs. If a pharmaceutical approach is not apparent from the protein function, one may be able to upmodulate gene expression at the level of transcription. This can be done by cloning the promoter region of the corresponding gene and analyzing the promoter sequence for the presence of cis elements known to provide the response to specific biological stimulators.

The most straightforward way to increase the expression of a drug sensitivity gene, identified through the GSE approach, would be to insert a full-length cDNA for such a gene into a gene therapy expression vector, for example, a retroviral vector. Such a vector, in the form of a recombinant retrovirus, will be delivered to tumor cells in vivo, and, upon integration, would sensitize such cells to the effects of the corresponding chemotherapeutic drug. A similar strategy for selective delivery of a drug-sensitivity gene into rat brain tumors, followed by curative treatment with the appropriate drug, was reported by Culver et al. (1992, *Science* 256: 1550–1552). The selective delivery to tumor cells can be accomplished on the basis of the selectivity of retrovirus-mediated transduction for dividing cells. Alternatively, the selectivity can be achieved by driving the expression of the drug sensitivity gene from a tissue- or tumor-specific promoter, such as, for example, the promoter of the carcinoembryonic antigen gene.

The protein structure deduced from the cDNA sequence can also be used for computer-assisted drug design, to develop new drugs that affect this protein in the same manner as the known anticancer drugs. The purified protein, produced in a convenient expression system, can also be used as the critical component of in vitro biochemical screen systems for new compounds with anticancer activity. In addition, mammalian cells that express cisplatin resistance-conferring GSEs according to the invention are useful for screening compounds for the ability to overcome drug resistance associated with down-regulation of the corresponding gene.

The following Examples are intended to further illustrate certain preferred embodiments of the invention and are not limiting in nature.

EXAMPLE 1

Generation of a Normalized Random Fragment cDNA Library in a Retroviral Vector A normalized cDNA population was prepared using a modification of the protocol described in abandoned U.S. patent application Ser. No. 08/033,086, filed Mar. 3, 1993, which is incorporated by reference. Briefly, poly(A)$^+$ RNA was purified from total RNA extracted from exponentially-growing cultures of human HeLa adenocarcinoma cells (subline S3). To avoid over-representation of the 5'-end sequences in a randomly primed cDNA population, RNA was fragmented by boiling for 5 minutes. These RNA fragments were then used for preparing randomly primed double-stranded cDNA. This randomly primed cDNA was then ligated to a synthetic adaptor providing ATG codons in all three possible reading frames and in a proper context for translation initiation (see FIG. 1). The structure of the adaptor determined its ligation to the blunt-ended fragments of the cDNA in such a way that each fragment started from initiation codons independently from its orientation. The ligated mixture was then size-fractionated by electrophoresis in a 6% polyacrylamide gel, and fragments ranging in size from approximately 200–600 basepairs (bps) were amplified by PCR, using the "senses" strand of the adaptor as a PCR primer. These PCRs were carried out in 23 separate reactions that were subsequently combined, to minimize random over- or under-amplification of specific sequences and to increase the yield of the product.

For normalization, the cDNA preparation was denatured and reannealed, using the following time-points for reannealing: 0, 24, 48, 72, 96 and 120 hours. The single-stranded and double-stranded DNAs from each reannealed mixture were then separated by hydroxyapatite chromatography. These DNA fractions from each time point of reannealing were PCR-amplified using adaptor-derived primers and analyzed by slot blot hybridization with probes corresponding to genes expressed at different levels in human cells. α-tubulin and c-myc probes were used to represent highly-expressed genes, adenosine deaminase and topoisomerase-II (using separate probes for the 5' and 3' ends of the latter cDNA) probes were used to represent intermediately-expressed genes, and a c-fos probe was used to represent low-level expressed genes. The greatest relative enrichment for low-level expressed genes was found in the single-stranded DNA fraction obtained after 120 hours of reannealing. This fraction was operationally defined as normalized and was re-amplified by PCR. The re-amplified DNA was then purified by gel electrophoresis, digested with ClaI, size-fractionated by gel electrophoresis, and 200–600 bp fragments were used for constructing a random-fragment normalized cDNA library.

Figure 2:
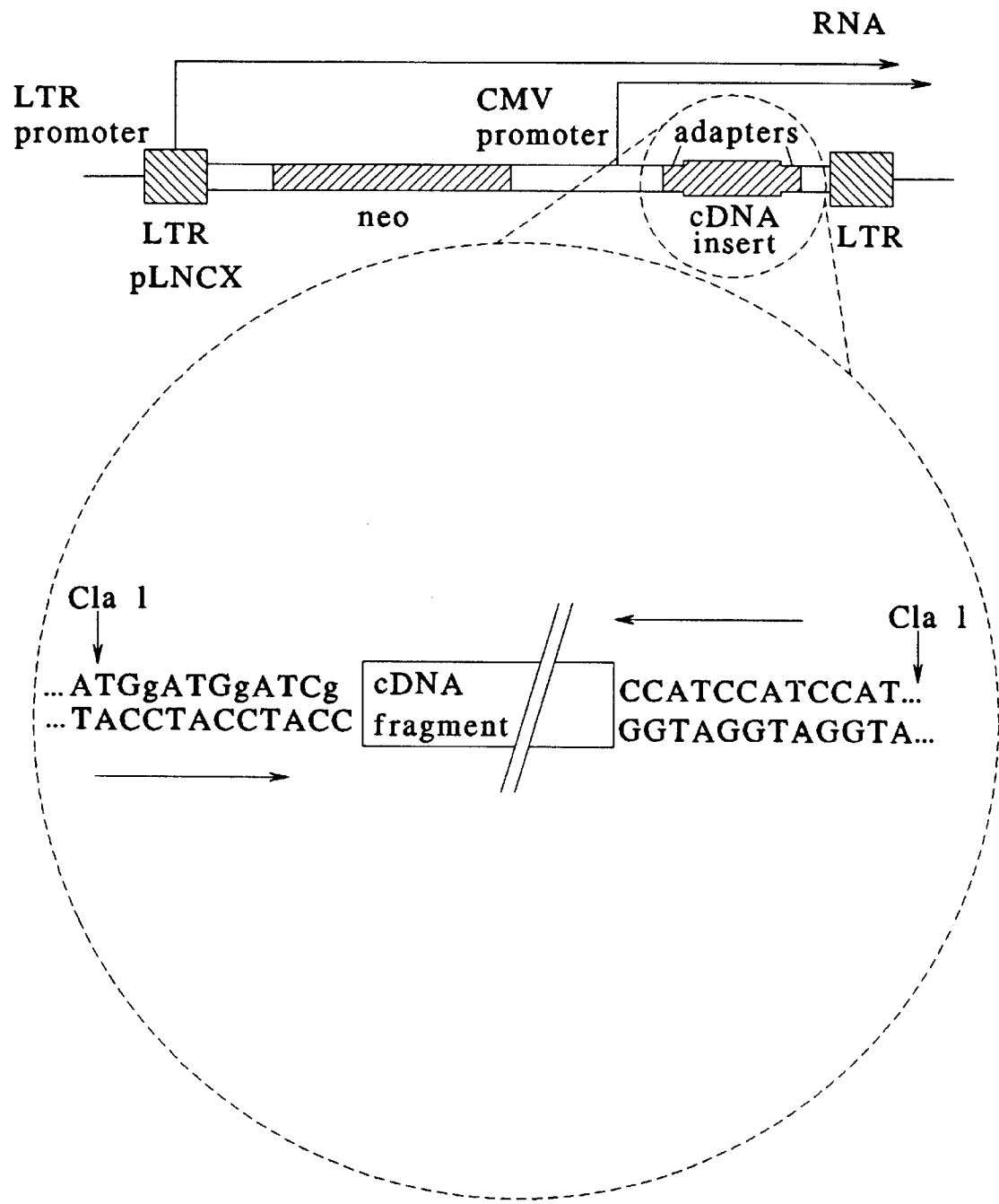
FIG. 2 shows the structure of the pLNCX vector used in cDNA cloning.

The normalized cDNA preparation was cloned into a ClaI site of the MoMLV-based retroviral vector pLNCX, which carries the neo (G418 resistance) gene, expressed under the transcriptional control of the promoter contained in the retroviral long terminal repeat (LTR), and which expresses the cDNA insert sequences from a cytomegalovirus (CMV)-derived promoter (see FIG. 2 and Miller and Rosman, 1989, *Biotechniques* 7: 980–986). pLNCX contains translation termination codons in all three reading frames within 20 bp downstream of the cloning site. To generate a representative-size library for GSE selection, this ligation mixture was used to transform a recombination-deficient strain of *E. coli* (strain invaF') in 14 separate electroporation experiments, using conventional techniques and standard conditions for electroporation (see Sambrook et al., 1992, *Molecular Clon-* ing: A Laboratory Manual, Cold Spring Harbor Laboratory Press, Cold Spring Harbor, N.Y.). The results of these experiments are shown in Table I; a total of $2.3 \times 10^7$ independent clones were obtained. PCR analysis of 269 randomly-picked clones revealed that 70% contained cDNA inserts, thus providing a total library size of $1.6 \times 10^7$ recombinant clones. Plasmid DNA was isolated from colony-amplified libraries prepared from each of the independent electroporation experiments, and the yield of plasmid DNA from each fraction is also shown in Table I.

TABLE I

| Electroporation Number | Ampicillin-Resistant Colonies | mg Plasmid Preparation Yield |
|---|---|---|
| 1 | $1.6 \times 10^6$ | 0.38 |
| 2 | $4.8 \times 10^5$ | 0.92 |
| 4 | $1.5 \times 10^6$ | 2.7 |
| 5 | $2.0 \times 10^6$ | 1.8 |
| 6 | $1.6 \times 10^6$ | 2.0 |
| 7 | $2.3 \times 10^6$ | 1.8 |
| 8 | $1.7 \times 10^6$ | 1.66 |
| 9 | $1.8 \times 10^6$ | 1.61 |
| 10 | $1.7 \times 10^6$ | 1.75 |
| 11 | $1.0 \times 10^6$ | 1.65 |
| 12 | $1.4 \times 10^6$ | 2.05 |
| 13 | $1.9 \times 10^6$ | 1.75 |
| 14 | $1.6 \times 10^6$ | 1.91 |
| 15 | $2.7 \times 10^6$ | 2.26 |
| Total | $2.3 \times 10^7$ | 24.24 |

EXAMPLE 2

Introduction of a Retroviral Random Fragment Library into Virus-Packaging Cell Lines and Human Cells The plasmid library prepared according to Example 1 was used to isolate GSEs inducing cisplatin resistance in human cells in three separate experiments. In each of the experiments, the LNCX vector was used in place of the library as a negative control. In the first two of these experiments, DNA from libraries prepared from individual electroporation experiments (Experiments 6 and 9 in Table I) was transfected by calcium phosphate procedure at a total of 62.5 μg per plate, into cells of an amphotropic retrovirus-packaging cell line (Bender et al., 1987, J. Virol. 61: 1639–1646; Markowitz et al., 1988, Virology 167: 400–406), the cell having been seeded the day before transfection onto six P150 culture plates per experiment at a density of $0.75-2.5 \times 10^6$ cells per plate. The retrovirus-containing cell culture supernatant was collected at 24, 48 and 72 hours post-transfection and used to infect cultures of human HeLa cells. For these infection experiments, HeLa cells were plated in six P150 culture plates at a density of $1.25 \times 10^6$ cells per plate and infected after overnight growth by incubation in the presence of 4 μg/mL polybrene with 25 mL per plate of the filtered virus-containing supernatant from the transfected amphotrophic cells described above. Infection of these HeLa cell cultures was then repeated twice more at 24 hour intervals. Three days after the last infection, the infection efficiency was estimated by plating $10^4$ cells in each of three P100 culture plates, growing the cells in media containing 600 μg/mL G418 and determining the percentage of G418-resistant cells that arose from these cultures. Using this assay, 1–2% of the HeLa cells were found to have been infected in the above-described experiments.

Alternatively, in a third experiment, a 1:1 mixture of ecotropic and amphotropic packaging cell lines (Markowitz et al., 1988, Virology 167: 400–406), each plated at $1.25 \times 10^6$ cells per P150 plate in a total of 16 culture plates, was transfected with a pooled fraction of the combined plasmid library. Such a pooled population of library DNA was prepared by mixing individual DNA preparations from each of the 14 independent electroporation experiments described in Example 1 at a ratio corresponding to the number of clones in each fraction. The retroviral population was collected as described above and used to infect cells of the HT1080/pJET-2fTGH (clone 2a) cell line (provided by G. Stark, Cleveland Clinic Foundation, Cleveland, Ohio). These cells are a derivative of HT1080 human fibrosarcoma cells transfected with a plasmid capable of expressing the murine ecotropic receptor (Albritton et al., 1989, Cell 57: 659–666) in these cells and making them susceptible to infection with ecotropic retroviruses. These cells (further referred to herein as HT1080/ER cells) were plated at a density of $1.25 \times 10^6$ cells per plate in sixteen P150 culture plates and infected as described above. Infection efficiency analysis (carried out at a concentration of 400 μg/mL G418) indicated that 60% of the HT1080/ER cells were infected in this experiment.

EXAMPLE 3

Figure 3:
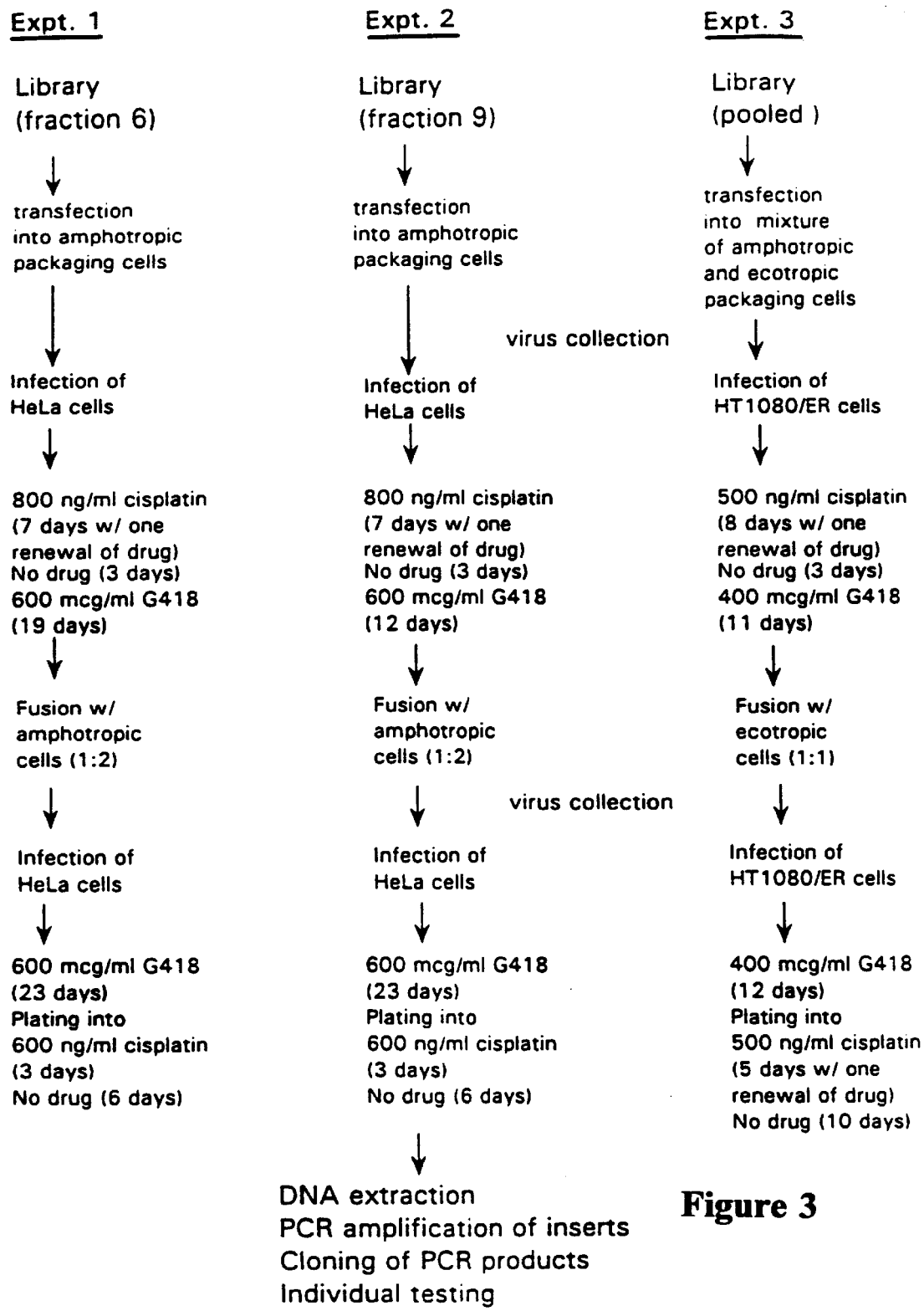
FIG. 3 shows a scheme for selection of cisplatin resistance-conferring GSEs from a random fragment expression library (RFEL) from HeLa cell cDNA.

Isolation of Cisplatin Resistance-Conferring GSEs by in vitro Cisplatin Selection of Human Cells Infected with a Retroviral Random Fragment Library Three days after the last round of infection with the retroviral cDNA fragment library, HeLa or HT1080/ER cells as described in Example 2 were plated in cisplatin-containing media at a concentration of cisplatin which produced approximately 99.9% cytotoxicity in unmodified cells. Selection with cisplatin was followed by G418 selection after growth for three days without any drug selection, using a protocol for each experiment shown in FIG. 3. Each protocol was followed using non-cDNA fragment-containing pLNCX retrovirus-infected cells as a control. After drug selection, increased survival of library-transduced cell populations, relative to the control cell populations, was apparent by microscopic examination in each of the three experiments.

Proviruses integrated into the genomes of library-transduced cells that survived selection were rescued by fusion of populations of such cells with amphotropic (for the first two experiments described above and in FIG. 3) or ecotropic (for the third experiment described above and in FIG. 3) virus packaging cells. Four independent fusions were performed using cells from the first experiment (designated H61, H62, H63 and H64), three independent fusions were performed using cells from the second experiment (designated H91, H92 and H93), and eight independent fusions were performed using cells from the third experiment (designated HL1–HL8). For fusion, the selected cells were mixed at ratios of 1:1 or 1:2 with packaging cells. After overnight growth, the cells were rinsed three times with phosphate-buffered saline (PBS; Sigma Chemical Co., St. Louis, Mo.) and then treated with a solution of 50% polyethylene glycol (M.W. 1,300–1,600; Sigma) for one minute at room temperature. Cells were then rinsed four times with serum-free Dulbecco's Modifiedd Eagle's Medium (DMEM) and then cultured under standard conditions.

Retroviral particles in the supernatant of the fused cell cultures were collected at 24 and 48 hours after fusion and used to infect HeLa cells (for the first two experiments) or HT1080/ER cells (for the third experiment). The infected cells were then selected with G418 and subsequently with cisplatin, using the protocol illustrated in FIG. 3. Most of the fusion-derived retroviral populations produced a clear increase in survival in the presence of cisplatin, relative to control cells transduced with insert-free virus.

EXAMPLE 4

Isolation of GSEs Conferring Resistance to the Chemotherapeutic Drug Cisplatin

Figure 4A:
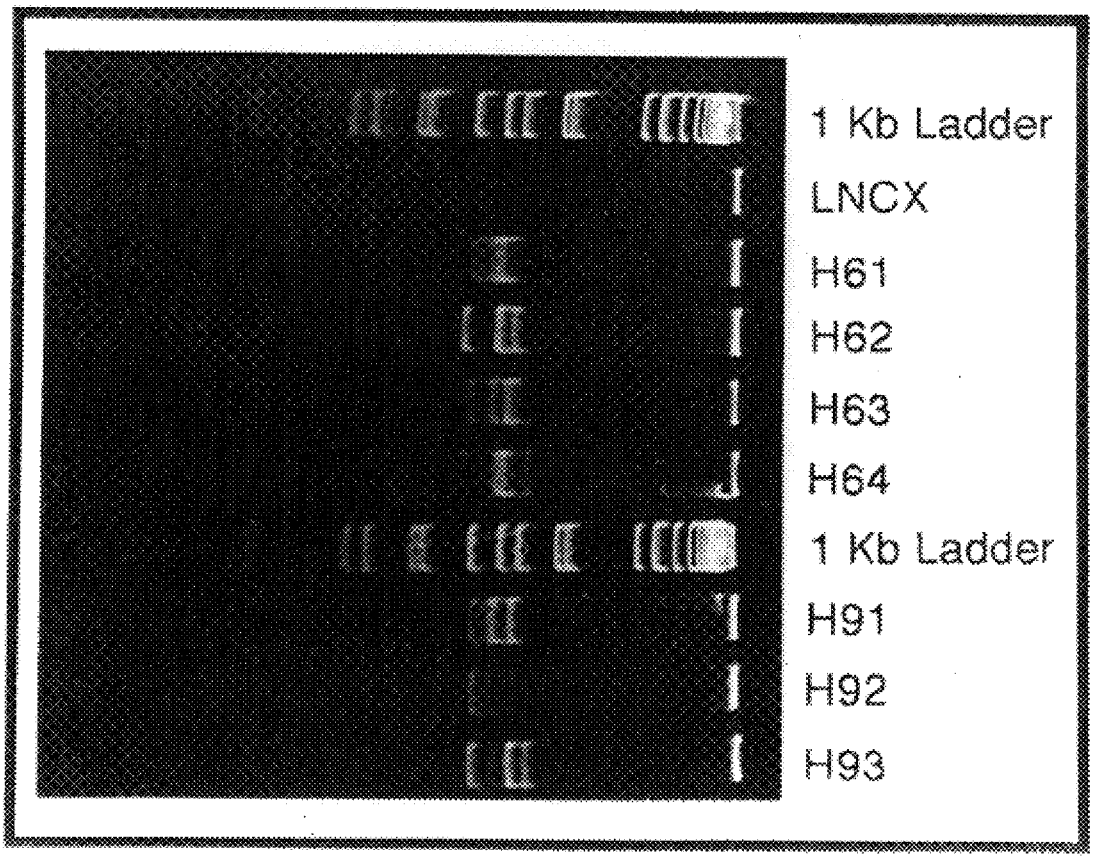
Figure 5A:
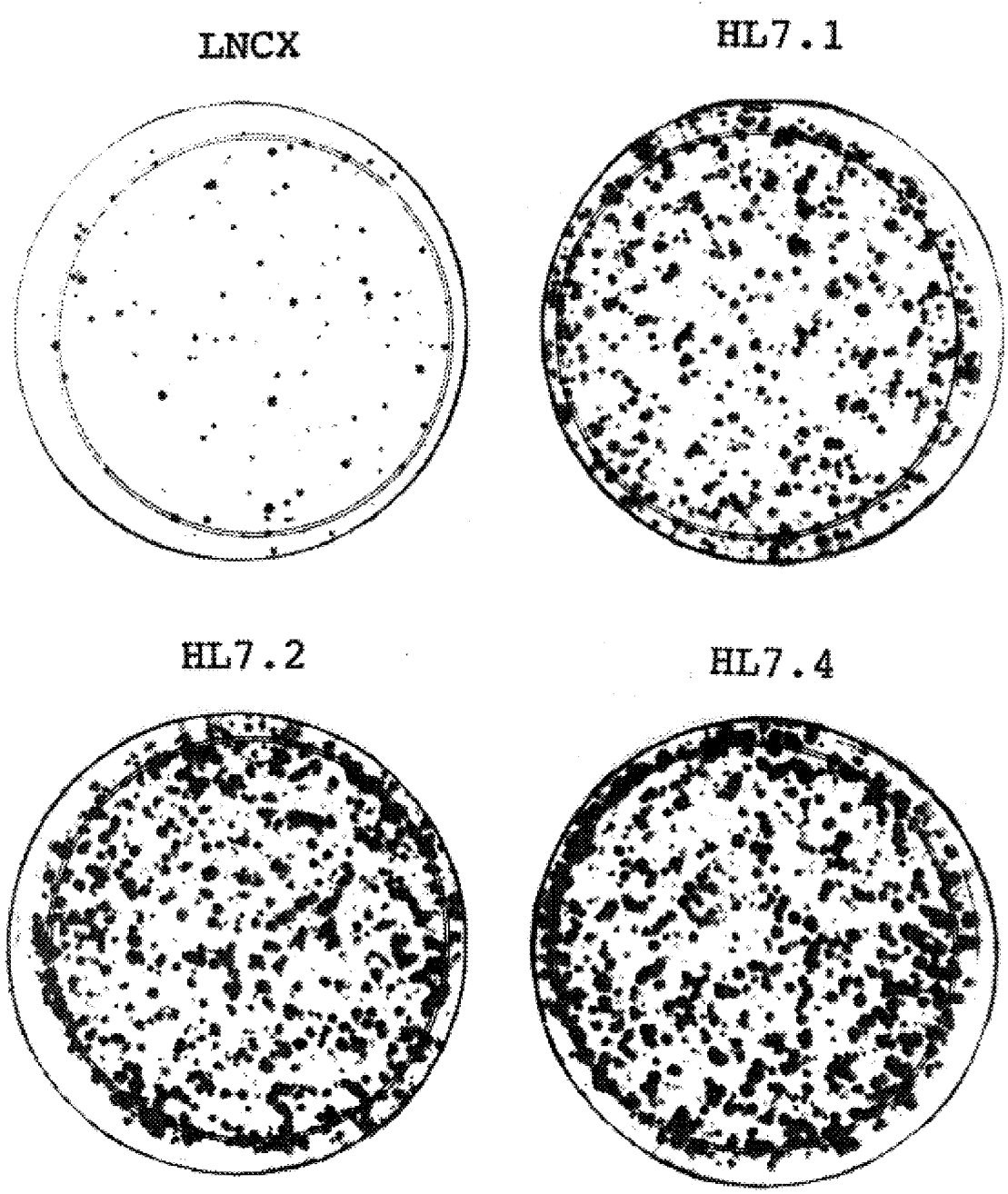
Figure 5B:
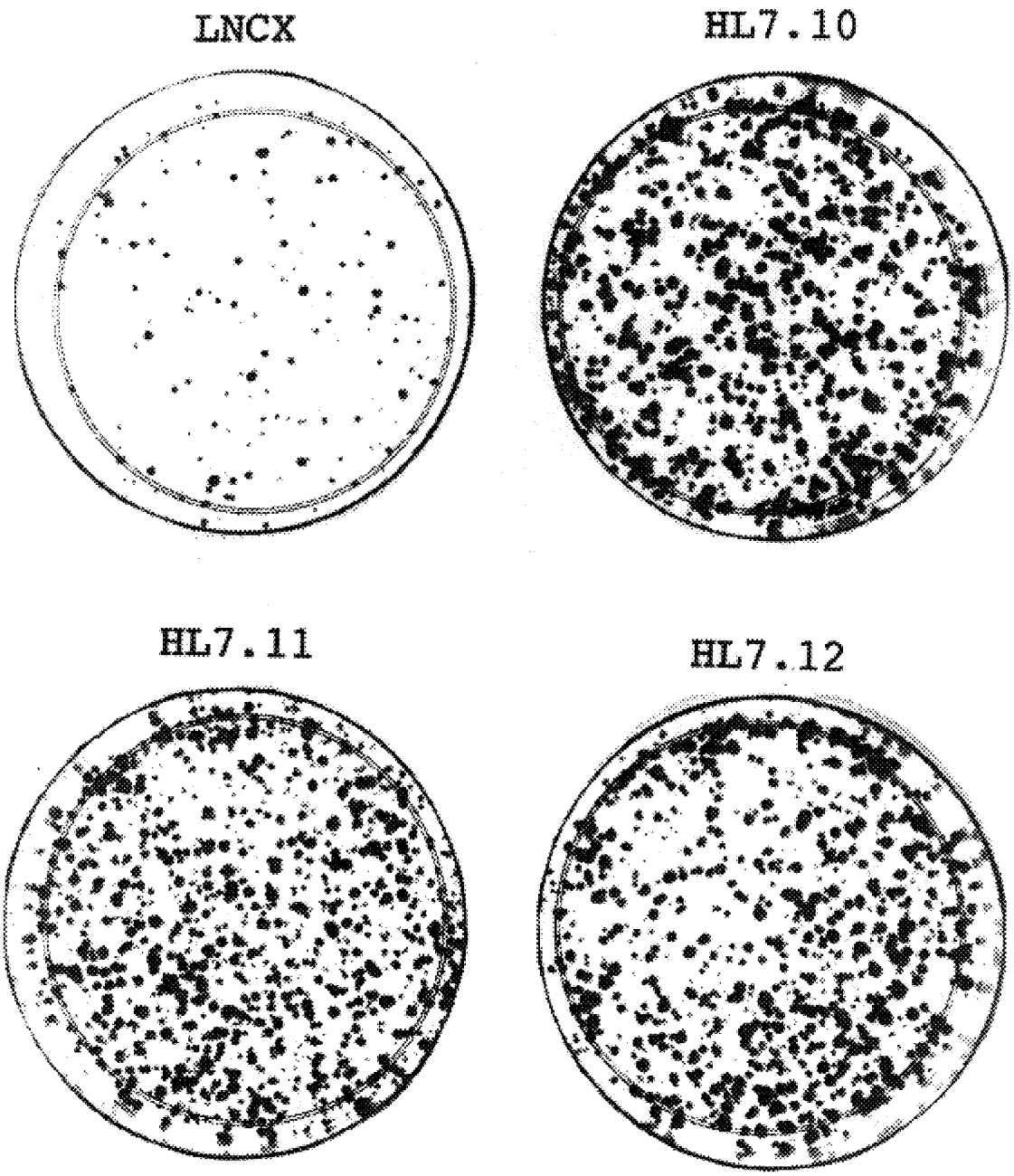

DNA was extracted using conventional techniques from each of the cell populations that were infected with fusion cell-derived retrovirus showing increased cisplatin resistance, as described in Example 2. The proviral inserts present in each of the corresponding populations of cell-derived DNAs were recovered by PCR amplification as described in abandoned U.S. patent application Ser. No. 08/033,086, filed Mar. 3, 1993, incorporated by reference. Polyacrylamide gel electrophoresis analysis of the PCR-amplified insert fragments are shown in FIGS. 4A and 4B. This analysis showed that each of the cisplatin-selected populations had only a small number of insert fragments. Individual PCR-amplified fragments were recloned into the pLNCX vector in the same position and orientation as in the original plasmid as described above in Example 1. A total of 66 clones were thus obtained.

The cloned proviral inserts were first compared to each other on the basis of their electrophoretic mobility in a 6% polyacrylamide gel. Of these, six inserts having different electrophoretic mobilities and isolated from the first two selection experiments described in Example 2, were chosen for biological activity tests. Each plasmid was transfected into a mixed cell population containing equal numbers of ecotropic and amphotropic packaging cells, and the resulting virus-containing supernatant used to infect HT1080/ER cells. After G418 selection of the transfected cells, each of the transduced cell populations was plated in P100 culture plates at a density of $2 \times 10^5$ cells per plate and grown in the presence of 500–700 ng/mL cisplatin, in triplicate cultures. Cells were incubated with the drug for 5 days, with the drug-containing media being renewed after three days incubation, and then the cells were grown for an additional 9–10 days in the absence of drug. The cell culture plates were then stained with crystal violet to detect the presence of drug-surviving cells.

The results of these experiments are shown in FIGS. 5A through 5G. Five of the six tested clones (termed H62.B2, H62.B5, H91.E2, H91.E2 and H93.G6) showed increased cisplatin resistance relative to control cells transduced with insert-free virus. The remaining clone, H62.B3 was scored as being negative in this assay. These results confirmed the identity of these inserts as cisplatin resistance-conferring GSEs.

These six GSEs were used as hybridization probes for slot blot hybridization analysis to determine which of the remaining 60 proviral inserts were different from these six GSEs. A total of twelve of the 60 inserts hybridized with these probes, and were withdrawn from further analysis.

The remaining 48 inserts were subjected to partial DNA sequence analysis to determine how many different sequences they contained. DNA sequencing reactions were performed on each insert specific for G and T nucleotides, and the pattern of the sequence ladders for each insert compared. As a result of these analyses, 30 of the 48 clones were found to be non-identical.

These 30 clones were then individually tested for their ability to confer cisplatin resistance on cells expressing each GSE. Each of the clones was transfected into a ecotropic virus packaging cell line, and virus-containing supernatants were collected 24 and 48 hours post-transfection were used to infect HT1080/ER cells. Infected cell populations were selected with G418 as described above to obtain populations in which all or almost all of the cells were infected with the retrovirus. These populations were then tested for cisplatin resistance by seeding nine P100 culture plates with $2 \times 10^4$ cells from each tested population and, one day later, exposing the cells to cisplatin at concentrations of 500, 600 and 700 ng/mL (in triplicate at each concentration). Cells were maintained under cisplatin selection for three days, incubated in drug-free media for an additional 9–10 days and then stained with crystal violet. Plating efficiency of each tested cell population was determined in parallel assays by plating 200 cells per P100 culture dish in drug-free media (in triplicate), as shown in FIG. 5.

Of the 30 clones tested, 10 showed the ability to confer cisplatin resistance on human cells. As shown in FIG. 5, these clones (H63.C8, HL4.1, HL6.1, HL6.10, HL7.1, HL7.2, HL7.4, HL7.10, HL7.11 and HL7.12) produced elevated levels of cisplatin resistance, confirming their identity as cisplatin resistance-conferring GSEs.

EXAMPLE 5

Isolation and DNA Sequence Analysis of GSEs Conferring Resistance to the Chemotherapeutic Drug Cisplatin The above-identified biologically-active GSEs were sequenced using a standard dideoxy sequencing protocol (see Sambrook et al., ibid.), and the sequences corresponding to each of these inserts are shown in FIGS. 6–20. The nucleotide sequences of both the "sense" and "antisense" strands of each of these clones, as well as the amino acid sequences of the peptides encoded by these strands in all three reading frames, were analyzed for homology to nucleic acid and protein sequences present in the National Center for Biotechnology Information databases, using BLASTN and BLASTX network programs for homology search (Altshul et al., 1990, *J. Mol. Biol.* 215: 403–410).

No significant homology was found with any known nucleic acid or protein sequence for the GSEs H62.B5 (SEQ ID NO:3), H63.C8 (SEQ ID NO:4), H91.E2 (SEQ ID NO:5), H93.G6 (SEQ ID NO:6), HL4.1 (SEQ ID NO:7), HL6.1 (SEQ ID NO:8), HL7.2 (SEQ ID NO:9), HL7.4 (SEQ ID NO:10), or HL7.12 (SEQ ID NO:12) (as shown in Table II). Homology between known sequences and the remaining six inserts, H62.B2, H91.E2, HL6.10, HL7.1, HL7.10 and HL7.11 was found. The results of sequence alignment between the six GSEs identified as being derived from known genes are shown in FIGS. 8 and 15–19 and include the following GSEs:

GSE HL6.10 (SEQ ID NO:13) is a sense-oriented fragment (see FIG. 20) of a previously-isolated cDNA encoding the XRCC1 gene (SEQ ID NO:17; X-ray repair cross-complementing-1; Thompson et al., 1990, *Mol. Cell. Biol.* 10: 6160–6171). This gene is known to correct defective DNA strand break repair and sister chromatid exchange. Although DNA damage is known to be a mechanism of cisplatin-mediated cytotoxicity (see Background of the Invention), so that DNA damage repair would be clearly important in cisplatin resistance, the types of DNA damage repaired by XRCC1 have not been previously associated with exposure to cisplatin.

GSE HL7.1 (SEQ ID NO:14) is a sense-oriented fragment (see FIG. 21) of a previously-isolated cDNA encoding the TRPM-2 gene (SEQ ID NO:18; testosterone-repressed prostatic message-2, also termed SGP-2 for sulfate glycoprotein-2; Buttyan, 1991, in *Apoptosis. The Molecular Basis of Cell Death*, Tomei & Cope, eds., Cold Spring Harbor Laboratory Press, Cold Spring Harbor, N.Y., pp. 157–173). This protein is known to be a common marker for programmed cell death (apoptosis) in different tissues (Buttyan, ibid.). Although apoptosis has been implicated in cisplatin cytotoxicity, the TRPM-2 gene, which is expressed at high levels even in some viable cells, has not been previously implicated directly in cisplatin-mediated cytotoxicity. Rather, due to its ability to inhibit complement-mediated cytolysis, this gene product was previously believed to protect cells in the surrounding tissue from non-specific complement-mediated cytolysis as the result of complement activation caused by apoptotic tissue turnover. The instantly-disclosed results demonstrated that TRPM-2 must play a more direct role in cisplatin-induced apoptosis.

GSE HL7.10 (SEQ ID NO:15) is a sense-oriented fragment (see FIG. 22) of a previously-isolated cDNA encoding phosphoglycerate mutase, isozyme B, non-muscle isoform (PGAM-B, SEQ ID NO:19; Sakoda et al., 1988, *J. Biol. Chem.* 263: 16899–16905), a glycolytic, "housekeeping" enzyme. Neither glycolysis nor the specific reaction catalyzed by this enzyme have been previously associated with cisplatin-mediated cytotoxicity.

GSE HL7.11 (SEQ ID NO:16) is an antisense-oriented fragment (see FIG. 23) of a previously-isolated cDNA encoding dihydroorotate dehydrogenase (DHOD, SEQ ID NO:20; Minet et al., 1992, *Gene* 121: 393–396). This enzyme catalyzes an intermediate step in the biosynthesis of uridylic acid (UMP) and deoxyuridylic acid (dUMP). It is known that the conversion of dUMP to TMP, catalyzed by thymidylate synthetase (TS) in conjunction with dihydrofolate reductase (DHFR) is a critical step in DNA synthesis, and provides a biochemical target for several anticancer drugs, including 5-fluorouracil and methotrexate. Changes in the intracellular folate pool have been associated with exposure to cisplatin, and some cisplatin-resistant cells have been reported to express increased amounts of both TS and DHFR (see Scanlon et al., 1986, *Proc. Natl. Acad. Sci. USA* 83: 8923–8927). Inhibition of DHOD by the antisense GSE disclosed herein would be expected to decrease the intracellular concentration of UMP and dUMP and thus affect the activity of TS and DHFR and the intracellular folate pool. These results support the hypothesis that folate pool perturbations and TS activity play a role in the cellular response to cisplatin, but provide a heretofore unexpected target for cisplatin sensitivity in tumor cells.

GSE H91.E2 (SEQ ID NO:17) is an antisense-oriented fragment (see FIG. 26) of a previously-isolated cDNA encoding human calcium/calmodulin (CaM) dependent protein kinase, isoform γB (CaMKGB, SEQ ID NO:21; Nghiem et al., 1993, *J. Biol. Chem.* 268: 5471–5479). The CaM kinase is known to mediate various effects of signal compounds that utilize $Ca^{++}$ as an intracellular second messenger. CaM kinase antagonists have been shown to potentiate the cytotoxicity of cisplatin, this effect being related to increased intracellular cisplatin accumulation in the presence of the antagonists (Kikuchi et al., 1992, *Gynecol. Oncol.* 39: 199–203). On the other hand, exposure to cisplatin has been reported to increase intracellular $Ca^{++}$ concentration (Kohnoe et al., 1992, *Anticancer Res.* 12(6B): 2203–2207), and such an increase has been implicated as a positive regulator of programmed cell death (McConkey et al., 1989, *Arch. Biochem. Biophys.* 269: 365–370). No specific isoforms of the CaM kinase have been previously reported to be associated with cisplatin sensitivity.

GSE H62.B2 (SEQ ID NO:12) is an antisense-oriented fragment (se FIG. 25) of a previously-isolated cDNA encoding human chondroitin/dermatan sulfate proteoglycan core protein PG40 (SEQ ID NO:22; Krusius & Ruoslahti, 1986, *Proc. Natl. Acad. Sci. USA* 83: 7683–7687), also known as decorin. Decorin is a ubiquitous small proteoglycan and a component of the extracellular matrix, which acts as a specific biological ligand for a number of proteins (see Iozzo & Cohen, 1993, *Experientia* 49: 447–455). Decorin is known to be capable of high affinity interactions with collagen Type I, Type II and Type VI, fibronectin, and transforming growth factor β (TGF-β). Tranfection of decorin cDNA into Chinese hamster ovary (CHO) cells has been reported to result in decreased cell density and increased growth inhibition (Yamaguchi & Ruoslahti, 1988, *Nature* 336: 244–246). These effects are believed to result from the ability of decorin to bind to and neutralize TGF-β, which is an autocrine growth factor for CHO cells (Yamaguchi et al., 1990, *Nature* 346: 281–284). Despite the multiplicity of biological and cellular effects reported for decorin, this protein has not been previously reported to be implicated in the cellular response to chemotherapeutic drugs, including cisplatin.

A summary of the cisplatin resistance-conferring GSEs identified herein is provided in Table II below.

TABLE II

| GSE Name | Length (nucleotides) | Corresponding Gene | Orientation |
|---|---|---|---|
| HL6.10 | 201 | XRCC1 | Sense |
| HL7.1 | 195 | TRPM-2 | Sense |
| HL7.10 | 188 | PGAM-B | Sense |
| H62.B2 | 122 | Decorin | Antisense |
| H91.E2 | 188 | CaMKGB | Antisense |
| HL7.11 | 238 | DHOD | Antisense |
| H63.C8 | 208 | Unknown | Unknown |
| HL4.1 | 200 | Unknown | Unknown |
| HL6.1 | 184 | Unknown | Unknown |
| HL7.2 | 178 | Unknown | Unknown |
| HL7.4 | 179 | Unknown | Unknown |
| HL7.12 | 212 | Unknown | Unknown |
| H62.B5 | 237 | Unknown | Unknown |
| H91.E2 | 221 | Unknown | Unknown |
| H93.G6 | 249 | Unknown | Unknown |

EXAMPLE 6

Cloning and Analysis of the Genes from which each Cisplatin-Resistance GSE was Derived The results described in Examples 4 and 5 above disclose the isolation of nine newly-identified genes implicated in cisplatin sensitivity in human tumor cells. Each of the genes corresponding to these nine GSEs are isolated as follows. Each GSE is used as a hybridization probe to screen a human cDNA library prepared from cisplatin-sensitive human tumor cells. The nucleotide sequence of the longest clone isolated in this way for each GSE is then determined, and the sequence analyzed to identify the longest open reading frame (ORF) encoding the putative gene product from each strand. Sequence homology analysis, as described above, is then performed on the sequence of the longest ORF to determine whether a related protein has been previously identified. If necessary, any additional nucleotides encoding amino acids from the amino terminus are then determined from 5'-specific cDNA isolated using the "anchored PCR" technique, as described by Ohara et al. (1989, Proc. Natl. Acad. Sci. USA 86: 5763–5677.) Additional missing 3' terminal sequences are also isolated using this technique. The "anchored PCR" technique can also be used to isolate full-length cDNA starting directly from the GSE sequence without library screening.

EXAMPLE 7

Generation of a Random Fragment cDNA Retroviral Library from Full-Length cDNA Corresponding to GSEs Conferring Cisplatin-Resistance The full-length cDNAs corresponding to novel and heretofore unidentified genes associated with cisplatin resistance as described in Example 5 above, as well as cDNAs corresponding to the six GSEs derived from known genes (CaMKGB, decorin, XRCC 1, TRPM-2, PGAM-B, and DHOD) are used to isolate and identify additional GSEs, including GSEs having an optimal ability to provide cisplatin resistance to human cells.

A library of random DNase I-generated fragments of any particular full-length human cDNA is generated essentially as described for topoisomerase II cDNA (see Example 1 in co-pending U.S. patent application Ser. No. 08/033,086, incorporated by reference) and the human KHCS kinesin gene (in co-pending U.S. patent application Ser. No. 08/177, 157, incorporated by reference). Specifically, two synthetic adaptors are used for ligation with DNase I-generated cDNA fragments. One adaptor, containing three ATG codons, carries a HindIII cloning site (see FIG. 9B of Ser. No. 08/177, 154). The other adaptor has translation stop codons in all three reading frames and carries a ClaI cloning site (see FIG. 9B of Ser. No. 08/177,154). After ligation with the equimolar mixture of both adaptors, cDNA fragments are amplified by PCR using sense and antisense strands of the first and second adaptor, respectively. PCR products are then digested with ClaI and HindIII and cloned into the corresponding sites of the pLNCX plasmid.

A plasmid library is obtained from this ligation mixture and is transfected into ecotropic packaging cells using the calcium phosphate precipitation technique. Virus released by transiently transfected cells is used to infect HT1080/ER. After infection and G418 selection, these cells are plated at $10^5$ cells per 100 mm plate and cultivated for 3 days in different concentrations of cisplatin (500–700 ng/mL). After removal of the drug, cells are allowed to grow in media without drug for 9–10 more days. At this point, some of the plates are fixed and stained with crystal violet, to determine the number of surviving colonies. DNA is prepared from populations of infected cells, and cisplatin resistance-associated inserts identified by PCR amplification as described above. Individual amplified fragments are tested for biological activity after being recloned into the pLNCX vector, and those fragments capable of providing cisplatin resistance to infected human tumor cells are isolated and their nucleotide sequence and expression orientation determined. Relative levels of cisplatin resistance capacity are determined by plating experiments in increasing concentrations of cisplatin, as described above and more generally in abandoned U.S. patent application Ser. No. 08/033,086, incorporated by reference.

It should be understood that the foregoing disclosure emphasizes certain specific embodiments of the invention and that all modifications or alternatives equivalent thereto are within the spirit and scope of the invention as set forth in the appended claims.

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

AATCATCGAT GGATGGATGG                                                   20

(2) INFORMATION FOR SEQ ID NO:2:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

```
CCATCCATCC ATCGATGATT AAA                                              23
```

(2) INFORMATION FOR SEQ ID NO:3:

(i) SEQUENCE CHARACTERISTICS:
    (A) LENGTH: 237 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:3:

```
AACTGGGGTC CCTTGGGGCG CCCCACGCTG CTTCCACACA CACCACCTCT GGCCTTGGGT      60
GGTGGCATTA CAGGGATGAG GGAGTCACTG TGGGTGGCCA CAGGGCTATG GCCAAGCGTT     120
CCCTGGCCGT CTTCCTCTGG CCTCAGCTTT GTTCCTATAG GCTGCCCGCG CCGTGGGCTG     180
CAGGTCTCGC CGCCCGCTTG ATCCCTGAGG TGTTTCCATG CTGCGGGTGG TGCTTCC        237
```

(2) INFORMATION FOR SEQ ID NO:4:

(i) SEQUENCE CHARACTERISTICS:
    (A) LENGTH: 206 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:4:

```
ATACACACAA ATTTACACAT GCAAACATGC ATGCACTGGG AAAAGATCTG CCCAATTGTA      60
TTAAACCATT TATGTTTCAG CCACAAAATT TCTAGTCTGT CACAGCTCTG GAGTCACCAG     120
AACCCTATCA TTTCACCAAC CCCACAGGGG CAAGCAACAT CTAGGAATCT GATTTTAATC     180
AGAGTTTCTT GATCTTCATC TGTTGC                                          206
```

(2) INFORMATION FOR SEQ ID NO:5:

(i) SEQUENCE CHARACTERISTICS:
    (A) LENGTH: 221 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:5:

```
GTGGAGTCCT GGGTGGAGGA TGGTCATTAC AAAGAGCAAG CCATCATTAC AACTTACAAG      60
CCCCAACCCT TGTGTGCTCT GGGGAGGTTA GAAGAGCTGG AGATTGAGTT AATAATCATG     120
CATGCCTGAG AAATGAAGCT CCATTTTGAA AAACCCCTAA AAGACAAAGT TTAGAGAGCT     180
ACTAGATTGG TGAACACATC TACGAGCTAT GAGGGTTGCT G                         221
```

(2) INFORMATION FOR SEQ ID NO:6:

(i) SEQUENCE CHARACTERISTICS:
    (A) LENGTH: 249 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:6:

```
GGCATAGAGT CCTGTTGGTT TTTTCTTCAC AAATGTTTTA TTTATCTGCT TTCATCACTA      60
ATCCCAATCT AGACTTCTTC ATGCCTGCTC ATTGCAAAAG CTCATCAGCT ATATTTTGCT     120
GATTCTAGAT TTTTTCCTTA TAATCTCTTC AGCAGAGCTG ACAACATAAT CTTGTTTAGT     180
TGCCACTTTG ACCACATTAT TCCTGCCCAA AATACCTTCA GTGACTTCCG TCTTCAGATC     240
AAATTCTTT                                                             249
```

(2) INFORMATION FOR SEQ ID NO:7:

(i) SEQUENCE CHARACTERISTICS:
        (A) LENGTH: 200 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
GCAGCTCCCT TGAACATGGA GGCCCCAGCG AGATGAGACC CCCACGAGAG GACTCTCGAC      60
CTCTACCCTG GTTACACATG CTTCTCATCC GCTCTCCAGC TTGGCGTGGA GCTCAGCAGC     120
AGGGAGCAGG TGTGAGGTGA GGTGCCACGC CTTGAGAAAC CCCAGGAATC GGCACACTGT     180
TCTCACGTAG CAGCCAGAGT                                                 200
```

(2) INFORMATION FOR SEQ ID NO:8:

(i) SEQUENCE CHARACTERISTICS:
        (A) LENGTH: 184 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
TCAGAATACA GTGATGAAAA TTCATTTTGA AACTCAAATA TTTTATTTTG GATATTCTCC      60
TGTTTTTATT AAACCAGTGA TTACACCTGG CCATCCCTCT AAATGTTCTA GGAAGGCATG     120
TCTATTGTGA TTTTGATGAA GACAGAATTA TTTTTCTCTG TAGAAACACA GATACCACTT     180
TATC                                                                  184
```

(2) INFORMATION FOR SEQ ID NO:9:

(i) SEQUENCE CHARACTERISTICS:
        (A) LENGTH: 178 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
GAATAATTGC AGGCCTGCGA CAGAGCTTGG CAGTGAGACA ACATTGCAAG CCGGGATACT      60
GCAACTCCCA ATACACTCCC TTCTTTGCTT GTTTTATACT CAATGTATGC CGGTTCTGTC     120
CCAGCAGGTG AGATGTGTGG CTGCCAGTCT TTCGGTGGCT TTGAAAGGTA CTTGGAAT      178
```

(2) INFORMATION FOR SEQ ID NO:10:

(i) SEQUENCE CHARACTERISTICS:
        (A) LENGTH: 179 base pairs
        (B) TYPE: nucleic acid
        (C) STRANDEDNESS: single

```
            (D) TOPOLOGY: linear (ii) MOLECULE TYPE: cDNA (xi) SEQUENCE DESCRIPTION: SEQ ID NO:10:

CTGAGGCCTG CCTGGGACCT GGAGACCTCC TGGGGTCAAT CTATCCACCT TGGGCCTTAT      60

GACCAATTGG GGCTTAAGGA TCTACTTAGA GACTGGTGTC AACCTGGAAC CTGGAACCTG     120

ATGTCCACTT GGAGTCTGGT GTACACCTTG GGCCTGATGC CACCTTGGCA CAGGTGTAC     179

(2) INFORMATION FOR SEQ ID NO:11:

(i) SEQUENCE CHARACTERISTICS:
        (A) LENGTH: 211 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

AGCCCTTTCA GTAACTATCA GGAGCCCTGA AACGGTAGAG GCACTGCCAT CCTTGTGGGA      60

TACTCAAAGC CCACAGGGCT TTTCCCTCCC TATTGCATCT TCTGATGCTC CCCACACCAC     120

CCTCCACCTC TCCACCTCTG TGGTGTTCCC ATTTGTGTGT TTCCCATCTG TGGAGCCAGA     180

CTGTTTGAGC AATAGCTTAG CAGCGAGTCA G                                    211

(2) INFORMATION FOR SEQ ID NO:12:

(i) SEQUENCE CHARACTERISTICS:
        (A) LENGTH: 122 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GGCAAGTTAT TTAGGAATGA GGAGGTGACA GCTGTAACTC AGTGTGGTTT TGCAGCTGCC      60

TACGTTAGTA CCAGGTATTC CATAAAACTC TGCAGAGGTC ATTTACATTT CGTAAATTCT     120

GT                                                                    122

(2) INFORMATION FOR SEQ ID NO:13:

(i) SEQUENCE CHARACTERISTICS:
        (A) LENGTH: 201 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CCCCGAGGAG AAGGCACCGA GCCCAGACGA TCCCGAGCTG GCCCAGAGGA GCTGGGGAAG      60

ATCCTTCAGG GTGTGGTAGT GGTGCTGAGT GGCTTCCAGA ACCCCTTCCA CTCCGAGCTG     120

CGAGATAAGG CCCTAGAGCT TGGGGCCAAG TATCGGCCAG ACTGGACCCG GGACAGCACG     180

CACCTCATCT GTGCCTTTGC C                                               201

(2) INFORMATION FOR SEQ ID NO:14:

(i) SEQUENCE CHARACTERISTICS:
        (A) LENGTH: 195 base pairs
        (B) TYPE: nucleic acid
        (C) STRANDEDNESS: single
```

(D) TOPOLOGY: linear (ii) MOLECULE TYPE: cDNA (xi) SEQUENCE DESCRIPTION: SEQ ID NO:14:

GCCAGGAGGA GCGCGCGGCA CAGGGTGCCG CTGACCGAGG CGTGCAAAGA CTCCAGAATT    60

GGAGGCATGA TGAAGACTCT GCTGCTGTTT GTGGGGCTGC CGCTGACCTG GGAGAGTGGG   120

CAGGTCCTGG GGGACCAGAC GGTCTCAGAC AATGAGCTCC AGGAAATGTC CAATCAGGGA   180

AGTAAGTACG TCAAT                                                   195

(2) INFORMATION FOR SEQ ID NO:15:

(i) SEQUENCE CHARACTERISTICS:
        (A) LENGTH: 188 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CAGCTACCCT CCTGTGAGAG TCTGAAGGAT ACTATTGCCA GAGCTCTGCC CTTCTGGAAT    60

GAAGAAATAG TTCCCCAGAT CAAGGAGGGG AAACGTGTAC TGATTGCAGC CCATGGCAAC   120

AGCCTCCGGG GCATTGTCAA GCATCTGGAG GGTCTCTCTG AAGAGGCTAT CATGGAGCTG   180

AACCTGCC                                                            188

(2) INFORMATION FOR SEQ ID NO:16:

(i) SEQUENCE CHARACTERISTICS:
        (A) LENGTH: 238 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

CCTCTCATGA TCCAGCCACA AAGGCTTGCC TGAGTCCTTG GGAAGGTTCC AGATCAGGCT    60

TCCCGTCAGA CGCTGTCCTC ACCTCCGATG ATCTGCTCCA ATGGCATCTG TGACTCCGCC   120

AAAGCCCTGC TCTTTCAGAA GGGTCTCCAG TTCCCGCTTG ACTTTGCCCA CAACGGGTGG   180

CCCCCAGAAG GTGAGGGCCG TGTACAGCTG TACCAGGGAG GCCCCTGCCC GGATCTTC    238

(2) INFORMATION FOR SEQ ID NO:17:

(i) SEQUENCE CHARACTERISTICS:
        (A) LENGTH: 187 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GTTCTGTAAT CTTAATGATC TCCTGTTTTC GCACTTTGAG GTCCTCATCT TCTGTGGTGG    60

TGTTGCAGCT CTCTGTGGAG CCCTTGATCC CATCTGTAGC GTTGTGTACC ACAGTGGTTG   120

TGGCTCCATG GCCGTCTGCA AGGGCACGGG CTCTTGGGCT GGGCTTACGA GACTGTTTTT   180

GTTGTTG                                                             187

(2) INFORMATION FOR SEQ ID NO:18:

(i) SEQUENCE CHARACTERISTICS:
            (A) LENGTH: 201 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:18:

CCCCGAGGAG AAGGCACCGA GCCCAGACGA CCCCGAGCTG GCCCAGAGGA GCTGGGGAAG      60

ATCCTTCAGG GTGTGGTAGT GGTGCTGAGT GGCTTCCAGA ACCCCTTCCG CTCCGAGCTG     120

CGAGATAAGG CCCTAGAGCT TGGGGCCAAG TATCGGCCAG ACTGGACCCG GGACAGCACG     180

CACCTCATCT GTGCCTTTGC C                                              201

(2) INFORMATION FOR SEQ ID NO:19:

(i) SEQUENCE CHARACTERISTICS:
            (A) LENGTH: 181 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:19:

CGCGGACAGG GTGCCGCTGA CCGAGGCGTG CAAAGACTCC AGAATTGGAG GCATGATGAA      60

GACTCTGCTG CTGTTTGTGG GGCTGCTGCT GACCTGGGAG AGTGGGCAGG TCCTGGGGGA     120

CCAGACGGTC TCAGACCATG AGCTCCAGGA AATGTCCAAT CAGGGAAGTA AGTACGTCAA     180

T                                                                    181

(2) INFORMATION FOR SEQ ID NO:20:

(i) SEQUENCE CHARACTERISTICS:
            (A) LENGTH: 188 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:20:

CAGCTACCCT CCTGTGAGAG TCTGAAGGAT ACTATTGCCA GAGCTCTGCC CTTCTGGAAT      60

GAAGAAATAG TTCCCCAGAT CAAGGAGGGG AAACGTGTAC TGATTGCAGC CCATGGCAAC     120

AGCCTCCGGG GCATTGTCAA GCATCTGGAG GGTCTCTCTG AAGAGGCTAT CATGGAGCTG     180

AACCTGCC                                                             188

(2) INFORMATION FOR SEQ ID NO:21:

(i) SEQUENCE CHARACTERISTICS:
            (A) LENGTH: 239 base pairs
            (B) TYPE: nucleic acid
            (C) STRANDEDNESS: single
            (D) TOPOLOGY: linear (ii) MOLECULE TYPE: cDNA (iv) ANTI-SENSE: YES (xi) SEQUENCE DESCRIPTION: SEQ ID NO:21:

CCTCTCATGA TCCAGCCACA AAGGCTTGCC TGAGTCCTTG GGAAGGTTCC AGATCAGGCT      60

TCCCGTCAGA CGCTGTCCTC ACCTCCGATG ATCTGCTCCA ATGGCATCTG TGACTCCGCC     120

AAAGCCCTGC TCTTTCAGAA GGGCCTCCAG TTCCCGCTTG ACTTTGCCCA CAACGGGTGG     180

```
GCCCCCAGAA GGGTAGGGCC GTGTACAGCT GCACCAGGGA GGCCCCTGCC CGGATCTTC         239

(2) INFORMATION FOR SEQ ID NO:22:

(i) SEQUENCE CHARACTERISTICS:
        (A) LENGTH: 188 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO:22:

CAACAACAAA AACAGTCTCG TAAGCCCAGC CCAAGAGCCC GCCCCCTTGC AGACGGCCAT        60

GGAGCCACAA ACCACTGTGG TACACAACGC TACAGATGGG ATCAAGGGCT CCACAGAGAG       120

CTGCAACACC ACCACAGAAG ATGAGGACCT CAAAGTGCGA AAACAGGAGA TCATTAAGAT       180

TACAGAAC                                                                188

(2) INFORMATION FOR SEQ ID NO:23:

(i) SEQUENCE CHARACTERISTICS:
        (A) LENGTH: 124 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO:23:

ACAGAATTTA CGAAATGTAA ATGACCTCTA CAGAGTTTTA TGGAATACCT GGTACTAACG        60

TAGGCAGCTG CAAAACCACA CTGAGTTACA GCTGTCAGCC CTCCTCATTC CTAAATAACT      120

TGCC                                                                    124
```

We claim:

1. A method of obtaining genetic suppressor elements that confer upon a cell in vitro resistance to platinum-based cytotoxic or cytostatic drugs, the method comprising the steps of:
   (a) synthesizing randomly fragmented cDNA prepared from the total mRNA of a cell to yield DNA fragments;
   (b) transferring the DNA fragments to an expression vector to yield a genetic suppressor element library, wherein each of the DNA fragments is operatively linked to a protein translation initiation codon, and wherein the expression vector expresses the DNA fragments in a living eukaryotic cell that is suceptible to inhibitory effects of a platinum-based cytotoxic cytostatic drug;
   (c) genetically modifying living eukaryotic cells by introducing the genetic suppressor element library into the living cells;
   (d) isolating or enriching for genetically modified living eukaryotic cells containing platinum-based growth-inhabitory drug resistance-conferring genetic suppressor elements by selecting cells in the presence of a platinum-based cytotoxic or cytostatic drug; and
   (e) obtaining the genetic suppressor element from the surviving genetically bodified eukaryotic cells.

2. A method according to claim 1, wherein the genetic suppressor element is a sense oriented genetic suppressor element encoding a peptide.

3. A method according to claim 1, wherein the genetic suppressor element is an antisense-oriented genetic suppressor element encoding an antisense RNA.

4. A method of isolating a gene associated with sensitivity to a platinum-based cytotoxic or cytostatic drug, comprising the step of screening a cDNA library with an oligonucleotide or polynucleotide having a nucleotide sequence of a GSE obtained by the method of claim 1.

5. A method of isolating a gene associated with sensitivity to a platinum-based cytotoxic or cytostatic drug, comprising the step of screening a genomic library with an oligonucleotide or polynucleotide having a nucleotide sequence of a GSE obtained by the method of claim 1.

6. The method of claim 4 wherein the GSE is selected from the group consisting of the GSEs H63.C8(SEQ ID NO:4) HL4.1 (SEQ ID NO:7), HL6.1 (SEQ ID NO:8), HL7.2 (SEQ ID NO:9), HL7.4 (SEQ ID NO:10), HL7.12 (SEQ ID NO:12), H62.B5 (SEQ ID NO:3), H91.E2 (SEQ ID NO:5), HL7.12 (SEQ ID NO:11), GSE HL6.10 (SEQ ID NO:13), GSE HL7.1 (SEQ ID NO:14) and H93.G6 (SEQ ID NO:6).

7. The method of claim 5 wherein the GSE is selected from the group consisting of the GSEs H63.C8(SEQ ID NO:4), HL4.1 (SEQ ID NO:7), HL6.1 (SEQ ID NO:8), HL7.2 (SEQ ID NO:9), HL7.4 (SEQ ID NO:10), HL7.12 (SEQ ID NO:12), H62.B5(SEQ ID NO:3), H91.E2 (SEQ ID NO:5), HL7.12 (SEQ ID NO:11), GSE HL6.10 (SEQ ID NO. 13), GSE HL7.1 (SEQ ID NO:14) and H93.G6 (SEQ ID NO:6).

8. An in vitro assay for detecting resistance to platinum-based drugs comprising the step of measuring expression of a gene comprising a nucleotide sequence of a GSE obtained according to the method of claim 1.

9. An in vitro assay for detecting resistance to platinum-based drugs comprising the step of measuring expression of a gene comprising a nucleotide sequence of a GSE selected from the group consisting of GSEs H63.C8(SEQ ID NO:4), HL4.1 (SEQ ID NO:7), HL6.1 (SEQ ID NO:8), HL7.2 (SEQ ID NO:9), HL7.4 (SEQ ID NO:10), HL7.12 (SEQ ID NO:12), H62.B5 (SEQ ID NO:3), H91.E2 (SEQ ID NO:5), HL7.12 (SEQ ID NO:11), GSE HL6.10 (SEQ ID NO:13), GSE HL7.1 (SEQ ID NO:14) AND H93.G6 (SEQ ID NO:6).

10. an isolated, genetically-engineered mammalian cell that expresses a GSE obtained according to the method of claim 1.

11. An isolated, genetically-engineered mammalian cell that expresses a GSE selected from the group consistion of the GSEs H63.C8(SEQ ID NO:4), HL4.1 (SEQ ID NO:7), HL6.1 (SEQ ID NO:8), HL7.2 (SEQ ID NO:9), HL7.4 (SEQ ID NO:10), HL7.12 (SEQ ID NO:12), H62.B5 (SEQ ID NO:3), H91.E2 (SEQ ID NO:5), HL7.12 (SEQ ID NO:11), GSE HL6.10 (SEQ ID NO:13), GSE HL7.1 (SEQ ID NO:14) AND H93.G6 (SEQ ID NO:6).

12. a method o obtaining genetic suppressor elements that confer upon a cell in vitro resistance to platinum-based cytotoxic or cytostatic drugs, the method comprising the steps of:
   (a) obtaining random DNA fragments of a gene associated with sensitivity to a platinum-based cytotoxic or cytostatic drug;
   (b) transferring the DNA fragments to an expression vector to yield a genetic suppressor element library, wherein each of the DNA fragment is operatively linked to a protein translation initiation codon, and wherein the expression vector expresses the DNA fragments in a living eukaryotic cell that is susceptible to inhibitory effects of a platinum-based cytotoxic or cytostatic drug;
   (c) genetically modifying living eukaryotic cells by introducing the genetic suppressor element library into the living cells;
   (d) isolating or enriching for genetically modified living eukaryotic cells containing platinum-based growth-inhibitory drug resistance-conferring genetic suppressor elements by selecting cells in the presence of a platinum-based cytotoxic or cytostatic drug; and
   (e) obtaining the genetic suppressor element from the surviving genetically modified eukaryotic cells.

13. A method according to claim 12, wherein the genetic suppressor element is a sender oriented genetic suppressor element encoding a peptide.

14. A method according to claim 12, wherein the genetic suppressor element is an antisense-oriented genetic suppressor element encoding an antisense RNA.

15. An isolated, genetically-engineered mammalian cell that expresses a GSE obtained according to the method of steps (a) through (c) of claim 12.

16. A GSE that confers upon a cell in vitro resistance to a platinum-based drug wherein the GSE is selected from the group consisting of the GSEs H63.C8(SEQ ID NO:4), HL4.1 (SEQ ID NO:7), HL6.1 (SEQ ID NO:8), HL7.2 (SEQ ID NO:9), HL7.4 (SEQ ID NO:10), HL7.12 (SEQ ID NO:12), H62.B5 (SEQ ID NO:3), H91.E2 (SEQ ID NO:5), HL7.12 (SEQ ID NO:11), GSE GL6.10 (SEQ ID NO:13), GSE HL7.1 (SEQ ID NO:14), AND H93.G6 (SEQ ID NO:6).

17. A method for conferring in vitro resistance to platinum-based drugs upon a cell, the method comprising introducing into the cell at least one of the GSEs according to claims 16.

18. An isolated, genetically-engineered mammalian cell made using the method of claim 17.

19. A method according to claim 1 wherein the platinum-based cytotoxic or cytostatic drug is a chemotherapeutic drug.

20. A method of identifying genetic suppressor elements that confer upon a cell in vitro resistance to platinum-based cytotoxic or cytostatic drugs, the method comprising the steps of:
   (a) synthesizing randomly fragmented cDNA prepared from the total mRNA of a cell to yield DNA fragments;
   (b) transferring the DNA fragments to an expression vector to yield a genetic suppressor element library, wherein each of the DNA fragments is operatively linked to a protein translation initiation codon, and wherein the expression vector expresses the DNA fragments in a living eukaryotic cell that is susceptible to inhibitory effects of a platinum-based cytotoxic or cytostatic drug;
   (c) genetically modifying living eukaryotic cells by introducing the genetic suppressor element library into the living cells;
   (d) isolating or enriching for genetically modified living eukaryotic cells containing platinum-based growth-inhibitory drug resistance-conferring genetic suppressor elements by selecting cells in the presence of a platinum-based cytotoxic or cytostatic drug;
   (e) obtaining the genetic suppressor element from the surviving genetically modified eukaryotic cells; and
   (f) identifying a nucleotide sequence of the genetic suppressor element obtained from the surviving genetically modified eukaryotic cells.

21. A method according to claim 20, wherein the genetic suppressor element is a sense oriented genetic suppressor element encoding a peptide.

22. A method according to claim 20, wherein the genetic suppressor element is an antisense-oriented genetic suppressor element encoding an antisense RNA.

23. An isolated, genetically-engineered mammalian cell that expresses a GSE obtained according to the method of claim 20.

24. A method of identifying genetic suppressor elements that confer upon a cell in vitro resistance to platinum-based cytotoxic or cytostatic drugs, the method comprising the steps of:
   (a) obtaining random DNA fragments of a gene associated with sensitivity to a platinum-based cytotoxic or cytostatic drug;
   (b) transferring the DNA fragments to an expression vector to yield a genetic suppressor element library, wherein each of the DNA fragments is operatively linked to a protein translation initiation codon, and wherein the expression vector expresses the DNA fragments in a living eukaryotic cell that is susceptible to inhibitory effects of a platinum-based cytotoxic or cytostatic drug;

(c) genetically modifying living eukaryotic cells by introducing the genetic suppressor element library into the living cells;

(d) isolating or enriching for genetically modified living eukaryotic cells containing platinum-based growth-inhibitory drug resistance-conferring genetic suppressor elements by selecting cells in the presence of a platinum-based cytotoxic or cytostatic drug;

(e) obtaining the genetic suppressor element from the surviving genetically modified eukaryotic cells; and (f) identifying a nucleotide sequence of the genetic suppressor element obtained from the surviving genetically modified eukaryotic cells.

25. A method according to claim 24, wherein the genetic suppressor element is a sense oriented genetic suppressor element encoding a peptide.

26. A method according to claim 24, wherein the genetic suppressor element is an antisense-oriented genetic suppressor element encoding an antisense RNA.

27. An isolated, genetically-engineered mammalian cell that expresses a GSE obtained according to the method of claim 24.

* * * * *